(12) United States Patent
Yang et al.

(10) Patent No.: US 12,133,893 B2
(45) Date of Patent: Nov. 5, 2024

(54) IN-SITU STABLE INJECTABLE COLLAGEN-BASED HYDROGELS FOR CELL AND GROWTH FACTOR DELIVERY

(71) Applicant: The Board of Trustees of the Leland Stanford Junior University, Stanford, CA (US)

(72) Inventors: Yunzhi Yang, Stanford, CA (US); Seyedsina Moeinzadeh, Mountain View, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 38 days.

(21) Appl. No.: 17/410,554

(22) Filed: Aug. 24, 2021

(65) Prior Publication Data
US 2022/0054639 A1    Feb. 24, 2022

Related U.S. Application Data

(60) Provisional application No. 63/069,347, filed on Aug. 24, 2020.

(51) Int. Cl.
| | | |
|---|---|---|
| A61K 47/42 | (2017.01) |
| A61K 9/00 | (2006.01) |
| A61K 9/06 | (2006.01) |
| A61K 35/28 | (2015.01) |
| A61K 47/02 | (2006.01) |
| A61K 47/36 | (2006.01) |

(52) U.S. Cl.
CPC ............ *A61K 47/42* (2013.01); *A61K 9/0019* (2013.01); *A61K 9/06* (2013.01); *A61K 35/28* (2013.01); *A61K 47/02* (2013.01); *A61K 47/36* (2013.01)

(58) Field of Classification Search
CPC ........ A61K 47/42; A61K 9/0019; A61K 9/06; A61K 35/28; A61K 47/02; A61K 47/36; A61L 27/26; A61L 27/50; A61L 27/52; A61L 27/38; A61L 2400/06
See application file for complete search history.

(56) References Cited

U.S. PATENT DOCUMENTS

| | | |
|---|---|---|
| 6,592,886 B1 | 7/2003 | Zimmermann |
| 7,588,938 B2 * | 9/2009 | Ma ...................... C12N 5/0062 435/368 |
| 9,610,328 B2 | 4/2017 | Mooney |

FOREIGN PATENT DOCUMENTS

WO    WO1999015211    4/1999

OTHER PUBLICATIONS

Lawson, et al., Adhesion and Growth of Bone Marrow Stromal Cells on Modified Alginate Hydrogels, Tisse Engineering, vol. 10, No. 9/10, 2004 (Year: 2004).*
Lee et al., Alginate: properties and biomedical applications, Prog Polym Sci. Jan. 2012; 37(1): 106-126 (Year: 2012).*
Zaheer Ali et al. Adjustable delivery of pro-angiogenic FGF-2 by alginate:collagen microspheres, Biology Open (2018) 7, bio027060 (Year: 2018).*
Jeanie L. Drury, The tensile properties of alginate hydrogels, Biomaterials 25 (2004) 3187-3199 (Year: 2004).*
Cattelan, G., Guerrero Gerbolés, A., Foresti, R., Pramstaller, P.P., Rossini, A., Miragoli, M. and Caffarra Malvezzi, C., 2020. Alginate formulations: current developments in the race for hydrogel-based cardiac regeneration. Frontiers in bioengineering and biotechnology, 8, p. 414. (Year: 2020).*
He et al. Integration of a Novel Injectable Nano Calcium Sulfate/ Alginate Scaffold and BMP2 Gene-Modified Mesenchymal Stem Cells for Bone Regeneration. Tissue Eng Part A. Feb. 2013; 19(3-4): 508-518.
Ghosh et al. Injectable Alginate-Peptide Composite Hydrogel as a Scaffold for Bone Tissue Regeneration. Nanomaterials (Basel). Apr. 2019; 9(4): 497.
Augst et al. "Alginate Hydrogels as Biomaterials." Macromol. Biosci. 6(2006):623-633.
Bidarra et al. Injectable alginate hydrogels for cell delivery in tissue engineering. Acta Biomaterialia vol. 10, Issue 4, Apr. 2014, pp. 1646-1662.

\* cited by examiner

*Primary Examiner* — Christopher M Babic
*Assistant Examiner* — Masudur Rahman
(74) *Attorney, Agent, or Firm* — LUMEN PATENT FIRM

(57) ABSTRACT

A stable injectable collagen-based hydrogel delivery platform and method is provided to obtain the viscosity, post-injection stability and mechanical properties needed of an injectable collagen matrix via incorporating alginate and calcium sulfate ($CaSO_4$) into the matrix. The hydrogel (Alg/Col hydrogel) is shear-thinning, injectable through commercially available needles and stable right after injection.

6 Claims, 22 Drawing Sheets

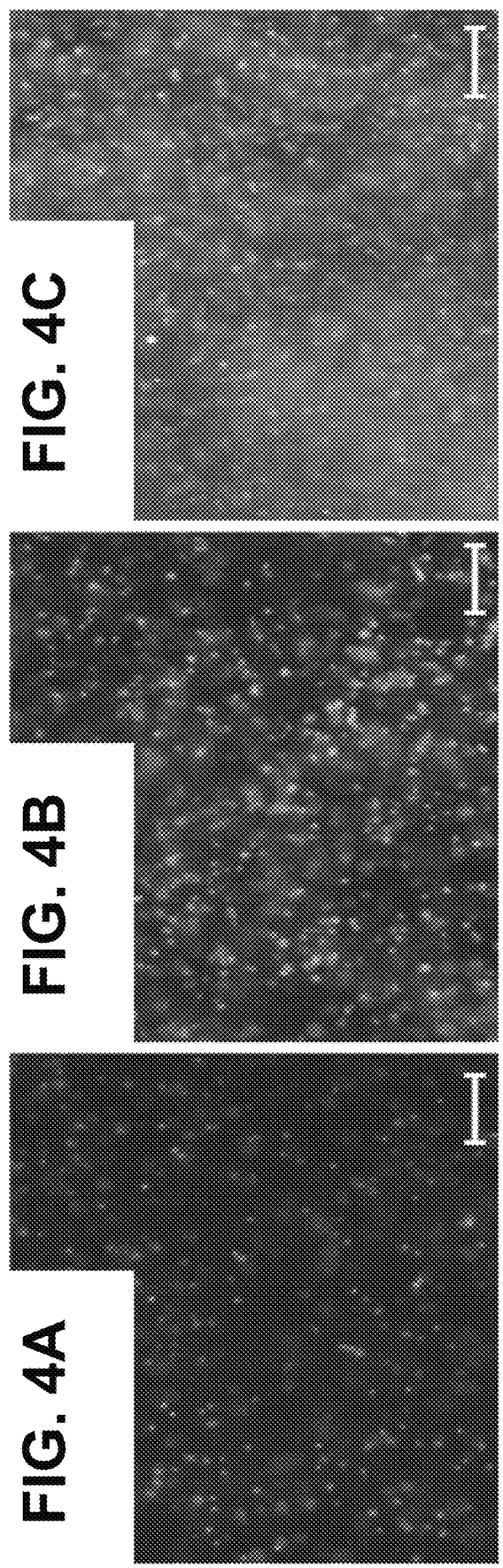

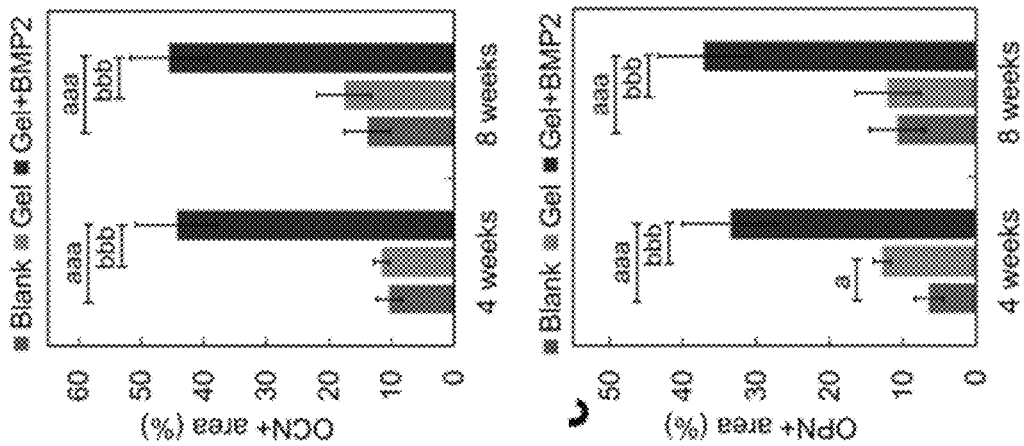
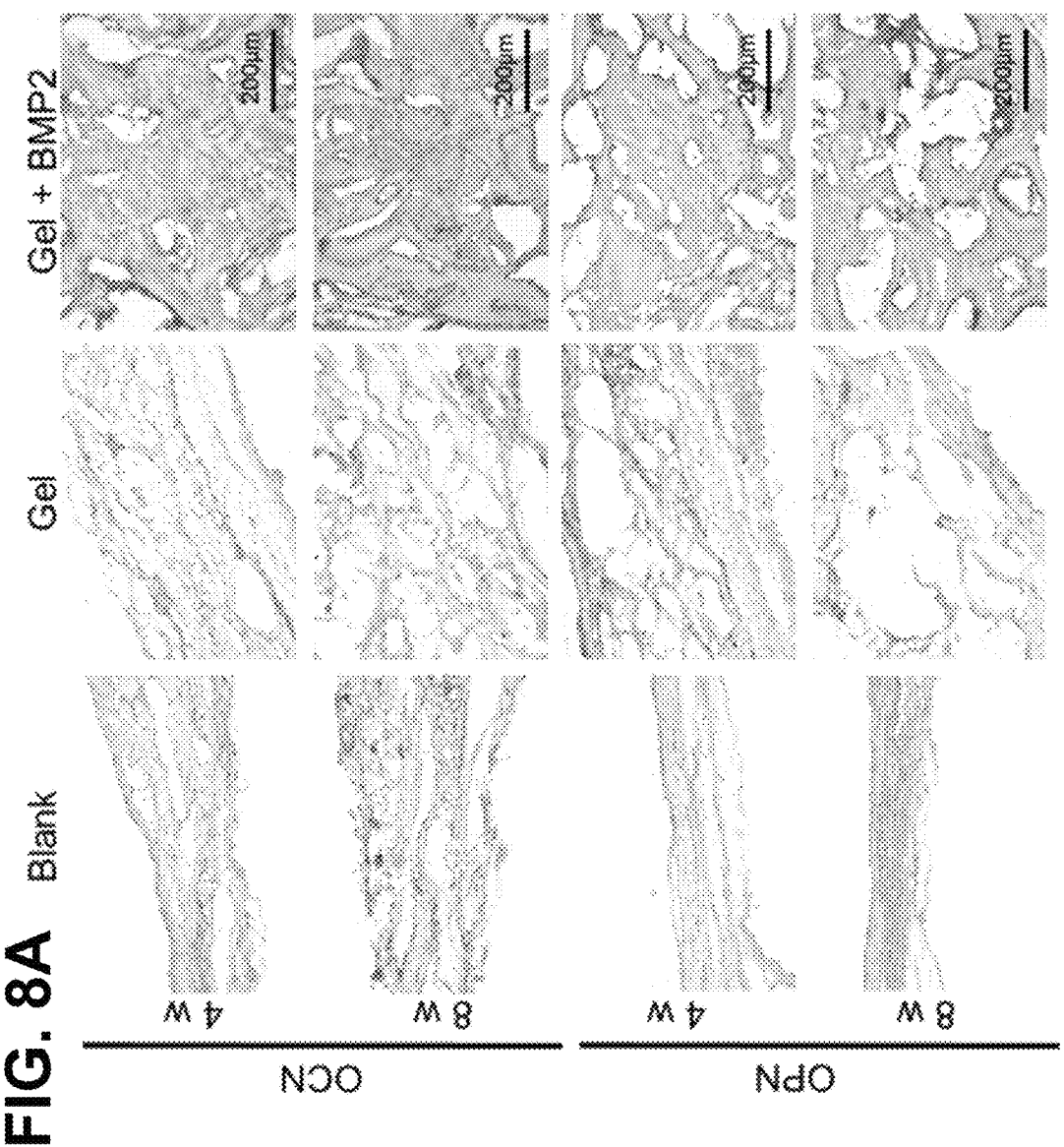

IN-SITU STABLE INJECTABLE COLLAGEN-BASED HYDROGELS FOR CELL AND GROWTH FACTOR DELIVERY

CROSS-REFERENCE TO RELATED APPLICATIONS

This application claims priority from U.S. Provisional Patent Application 63/069,347 filed Aug. 24, 2020, which is incorporated herein by reference.

STATEMENT OF GOVERNMENT SPONSORED SUPPORT

This invention was made with Government support under contract AR074458 awarded by the National Institutes of Health, and under contract AR069395 awarded by the National Institutes of Health. The Government has certain rights in the invention.

FIELD OF THE INVENTION

This invention relates to stable injectable collagen-based hydrogels.

BACKGROUND OF THE INVENTION

Injectable hydrogels have been used as carriers for therapeutic delivery, including cells and proteins to the defect site in regenerative medicine. Due to their large water content, porous microstructure and permeability to oxygen, nutrients, proteins and cell waste products, hydrogels provide a three-dimensional (3D) microenvironment for cell encapsulation. In addition, bioactive molecules can be incorporated into injectable hydrogels to promote cell adhesion, proliferation and differentiation of stem cells.

In-situ cross-linkable injectable hydrogels that are liquid before injection introduce some concerns such as that they are influenced by the in-vivo microenvironment prior to crosslinking, may leak from the defect site into the neighboring tissues, and dilute with the body fluid before gelation, or need additional stimuli such as light for crosslinking.

Shear-thinning injectable hydrogels, that are partially or fully crosslinked before injection, flow through syringe and needles under the applied shear stress and with that take the shape of the defect cavity. These pre-crosslinked shear-thinning hydrogels are relatively stable and don't leak out, yet they get diluted or washed away after injection. Further, due to a protective effect of hydrogel, cells delivered in pre-crosslinked shear-thinning hydrogels have higher viability following injection compared to the cells delivered in solutions. Therefore, shear-thinning hydrogels have recently been used not only as carriers for delivery of cells and therapeutics to the regeneration site, but also as bioinks for 3D bioprinting of tissues.

Alginate hydrogels are biocompatible and non-immunogenic hence good candidates for cell and therapeutics delivery. A typical method for making alginate gel is instantaneous crosslinking of alginate in the solutions of water-soluble salts of divalent cations (e.g. $CaCl_2$). The strong local crosslinks and inhomogeneity in the crosslink density of the alginate hydrogels prepared via this instantaneous gelation method though hinder the injectability and printability of the hydrogel.

Alginate hydrogels with improved crosslinking distribution and injectability have been made using divalent cation salts of low solubility including $CaSO_4$. Although injectable alginate hydrogels are biocompatible, they lack adhesive ligands that are required for cell survival, growth and proliferation within a 3D matrix. Modification of alginate molecule with cell adhesive peptides have been used to impart cell-adhesive ligands to alginate hydrogels, but short peptides lack the full function and specificity of native extracellular matrix (ECM) proteins.

Collagen is the most abundant protein component of the extracellular matrix (ECM) that contribute to the structure and function of tissues. Collagen directly interacts with multiple integrin receptors on the cell surface including $\alpha1\beta1$, $\alpha2\beta1$, $\alpha11\beta1$, and $\alpha V\beta3$ integrins, as well as discoidin domain receptor tyrosine kinases 1 and 2 (DDR1 and DDR2). In addition, collagen is indirectly sensed by cells through interaction with cell-binding proteins. The cell-collagen interaction has been shown to play a key role in regulation of cell adhesion, proliferation and differentiation. For example, the survival and osteogenic differentiation of hMSCs in collagen type I depend on interactions between collagen and both $\alpha2\beta1$ and $\alpha11\beta1$ integrins. Due to the unique properties of collagen, collagen-based hydrogels mimic the native tissue microenvironment and have been used as 3D scaffolds for cell encapsulation in tissue engineering applications. Crosslinked collagen hydrogel is not injectable whereas uncrosslinked collagen hydrogel precursor solution is an injectable liquid and has been used for delivery of cells in regenerative medicine.

However, as mentioned above, cell delivery in liquid formulations suffers from potential dilution and leakage to neighboring tissues due to a lack of stability in the target site. Also, a low viscosity and inferior structural stability of collagen precursor solution, limits its application as bioink in 3D bioprinting. A number of strategies such as mixing pre-assembled collagen fibrils with injectable alginate hydrogel, or exposing the alginate/collagen mixtures to $Ca^{2+}$ solution have been tested to increase the stability of collagen-based hydrogel following injection and to tune the physicomechanical characteristics of hydrogel. However, these methods need collagen fibrils preprocessing steps or special instrumentation such as coaxial nozzles or luer-lock syringes.

The present invention addresses these shortcomings, problems and/or concerns to advance the art with in-situ stable injectable collagen-based hydrogels for cell and growth factor delivery.

SUMMARY OF THE INVENTION

Definitions

Growth Factors are defined as biomolecules that can regulate and stimulate cell functions such as cell proliferation, differentiation, tissue development and regeneration. Examples are: Bone morphogenic proteins (BMPs) and Transforming Growth Factor βs (TGF-βs).

Biologics are defined as live cells or biomolecules Examples are: mesenchymal stem cells (MSCs), proteins, peptides, mRNA.

Therapeutics are defined as molecules that are used for treatment of a medical condition such as disease or trauma, etc. Examples are bisphosphonates and antibiotics.

Shear-thinning is defined as a reduction of viscosity under shear strain.

Calcium-free DMEM medium is defined as Dulbecco's Modified Eagle Medium (DMEM) without calcium salts or $Ca^{2+}$ ions. Although the inventors in their exemplary embodiments used calcium-free DMEM, any other type of calcium-free medium could be used for synthesizing the gel.

Partially cross-linked alginate is defined as alginate/calcium solution with shear-thinning properties and with its storage modulus (G') higher than the storage modulus of pure alginate solution but its G' lower than the peak G' associated with fully crosslinked alginate.

A Basic Medium is defined as a medium with pH higher than physiological pH (7.4).

An Acidic Medium is defined as a medium with pH lower than physiological pH (7.4).

The calcium free and basic pH medium is defined as a medium without calcium ions or calcium-based salts and with pH higher than physiological pH (7.4).

The calcium free and acidic medium is defined as a medium without calcium ions or calcium-based salts and with pH lower than physiological pH (7.4).

Stable is defined as not flowing away from the injection site or diffusing into neighboring environment after being injected.

Ratios are defined as the volume (or weight) ratio of one material to the volume (or weight) of another material. Concentrations are defined as the weight of a material in a unit volume of a solvent or solution.

This invention provides an in-situ stable injectable collagen-based hydrogel for delivery of cells, growth factors and/or other bioagents such as antibiotics or analgesics in regenerative medicine, drug delivery or bioprinting.

Collagen solution is an injectable liquid that crosslinks at 37 degrees Celsius and physiological pH and loses its injectability following crosslinking. A potential dilution with body fluid, leakage to neighboring tissues and a chance of being washed away before gelation limit the use of uncrosslinked collagen solution for cell and/or protein delivery in regenerative medicine. In addition, a low viscosity and inferior structural stability of collagen precursor solution, limits its application as bioink in 3D bioprinting.

The inventors developed an in-situ stable injectable collagen-based hydrogel, and a method to obtain the viscosity, post-injection stability and mechanical properties needed of an injectable collagen matrix via incorporating alginate and calcium sulfate ($CaSO_4$) into the matrix. The hydrogel (Alg/Col hydrogel) is shear-thinning, injectable through commercially available needles and stable right after injection.

The invention is a collagen hydrogel including partially cross-linked alginate as a delivery platform for cells, growth factors and/or other bioagents such as antibiotics or analgesics in regenerative medicine, drug delivery or bioprinting. The invention is also a medical delivery platform having:

An alginate precursor solution (first precursor) wherein alginate is dissolved in calcium free DMEM and supplemented with 1N NaOH to make alginate precursor solution. The normality of NaOH could range between 0.1N to 5N. The amount of NaOH depends on the concentration of collagen. I defined a range for collagen concentration below. The alginate precursor solution is a viscous solution that contains uncrosslinked alginate in a basic medium, and A collagen and $CaSO_4$ precursor solution (second precursor) wherein collagen is dissolved in calcium-free DMEM (or other calcium-free mediums or buffers) and supplemented with $CaSO_4$ to make collagen precursor solution. The collagen precursor solution is a solution that contains uncrosslinked collagen and suspended CaSO4 in an acidic medium.

These two precursors can then be mixed after adding cells, growth factors and/or other bioagents to the second precursor solution (or alternatively to the first precursor) and can then be injected into a subject. The invention is also a method of making the precursors and mixed composition.

Alginate Precursor Solution

Alginate is dissolved in calcium free Dulbecco's Modified Eagle Medium (DMEM, high glucose, no glutamine, no calcium; purchased from Thermo Fisher Scientific) medium, at 1-3% (w/v) concentration, filtered using a 0.22 μm PES filter and supplemented with 1N NaOH (a range of 0.1N to 5N could be used). The amount of added NaOH depends on alginate to collagen ratio. The alginate to collagen weight ratio (Alg/Col ratio) could range from 1/10 to 10/1. The alginate solution is sterilized by filtration using 0.22 micrometer Millex syringe filters and stored at 4° C. Alginate precursor solution may be supplemented with collagen crosslinkers. Some examples are linear or star polyethylene glycol succinimidyl carboxymethyl ester. Alginate could be modified to crosslink using photoinitiators or cross-react with collagen. The alginate precursor solution is red-violet color viscous solution that contains uncrosslinked alginate in a basic medium.

Collagen and CaSO4 Precursor Solution

Calcium sulfate (CaSO4) is sterilized using electron beam. Deionized (DI) water is sterilized using a 0.22 micrometer PES filter. 1 mL sterile DI water is then added to 100 mg sterile CaSO4 and the suspension is vortexed for 5 minutes. Calcium free DMEM medium is added to collagen at 4° C. The concentration of collagen in the precursor solution is adjustable. The concentration of collagen in the precursor solution could range from 1 mg/mL to 100 mg/mL. Then, the collagen solution is supplemented with vigorously vortexed CaSO4 suspension and mixed via pipetting to make collagen precursor solutions. The amount of added $CaSO_4$ could be changed. The concentration of $CaSO_4$ in the collagen precursor solution could range from 1 to 10 mg/mL.

Mixing Both Precursors

The collagen and $CaSO_4$ precursor solution is added to the alginate precursor solution (precursor 1) at a close to 1:1 volume ratio and pipetted multiple times. One could define a wider range for the ratio of precursor solutions here, e.g. from 1:10 to 10:1. As discussed infra this ratio could be changed, if the pH and CaSO4 concentration are adjusted. The volume ratio of precursor 2 to precursor 1 could change, if the pH of precursor 1 and concentration of CaSO4 in precursor 2 are adjusted. It is noted that if the volume range changes, the pH of precursor 1 and the concentration of $CaSO_4$ in precursor 2 need to be adjusted as a skilled artisan would appreciate. A syringe and needle can be used to transfer one precursor solution into other precursor solution container/vials and mix the two precursor solutions multiple times. When alginate is exposed to CaSO4 in the mixture, it crosslinks and forms a gel. However, the alginate crosslinking is partial and the gel is injectable because the concentration of $CaSO_4$ in the collagen and $CaSO_4$ precursor solution is low (1-10 mg/mL). If higher concentration of $CaSO_4$ in collagen and $CaSO_4$ precursor solution (>15 mg/mL) is used, the gel becomes inhomogeneous and uninjectable. Uncrosslinked collagen in the injectable gel crosslinks at 37° C. after injection.

More specifically, alginate crosslinking is through $Ca^{2+}$ ions that are dissolved in the collagen and $CaSO_4$ precursor solution. The dissolution of calcium and diffusion of $Ca^{2+}$ ions occurs on the surface of the salt particles. In the presence of alginate chains that have a high density of negative charge, the calcium ions may not diffuse far from the salt surface and only crosslink the local alginate chains. Therefore, when one increases the salt concentration the density of these local crosslinks increases. When the increase of the salt concentration reaches certain level of local crosslinks, the gel become inhomogeneous and uninjectable. Also, collagen molecules are able to chelate the calcium ions and make physical bonds to alginate chains through ion bridges.

It is worth noting that the use of $CaSO_4$ is an exemplary embodiment of salts of bivalence or multiple valences. Other examples include sulfate salts such as $MgSO_4$, Sr, Ba, Al or $Ti^{4+}$ or other non-insoluble salts. The general process remains the same. However, concentrations of components and the ratio of the precursor solution needs to be tuned as a skilled artisan would readily appreciate. These bivalence or multiple valence ions may dissolve from the salts and diffuse into surrounding aqueous environments and locally crosslink the alginate hydrogel and form ionic bridge between alginate network and collagen networks. Therefore, and alternatively, $CaSO_4$ could be substituted with other double and/or multiple valence ions to obtain the same objective of partially crosslinking which is important in the embodiments of this invention. Another aspect that should be kept in mind that any substitutes of $CaSO_4$ should be as "cell-friendly" as $Ca^{2+}$ ions. A variation could be considered to have combinations of Ca and other ions.

Method of Making

The following is an exemplary embodiment for the making of an Alg/Col hydrogel, in which alginate is dissolved in calcium free Dulbecco's Modified Eagle Medium (DMEM, high glucose, no glutamine, no calcium; purchased from Thermo Fisher Scientific) medium, at 1-3% (w/v) concentration, filtered using a 0.22 um PES filter and supplemented with IN NaOH. The amount of added NaOH depends on alginate to collagen ratio. The alginate to collagen weight ratio (Alg/Col ratio) could range from 1/10 to 10/1. The alginate solution is sterilized by filtration using 0.22 micrometer Millex syringe filters and stored at 4° C. Alginate precursor solution may be supplemented with collagen crosslinkers, including linear or star polyethylene glycol succinimidyl carboxymethyl ester. Alginate could be modified to crosslink using photoinitiators or cross-react with collagen. Calcium sulfate ($CaSO_4$) is sterilized using electron beam. Deionized water is sterilized using a 0.22 micrometer PES filter. 1 mL sterile DI water is then added to 100 mg sterile $CaSO_4$ and the suspension is vortexed for 5 minutes. Calcium free DMEM medium is added to collagen at 4° C. The concentration of collagen in the precursor solution is adjustable. Then, the collagen solution is supplemented with vigorously vortexed $CaSO_4$ suspension and mixed via pipetting to make collagen precursor solutions. The amount of added $CaSO_4$ could be changed. The concentration of $CaSO_4$ in the collagen precursor solution could range from 1 to 10 mg/mL. The collagen precursor solution is added to the alginate solution at 1:1 volume ratio and pipetted multiple times. A syringe and needle can be used to transfer one precursor solution into other precursor solution container/vials and mix the two precursor solutions multiple times. Pre-crosslinked Alg/Col hydrogels fully crosslink at 37° C. and the storage modulus and viscosity of Alg/Col hydrogels are tunable in the 20-1600 Pa and 8-800 Pa·S range, respectively with adjusting the collagen content or the concentration of $CaSO_4$. Model stem cells (human mesenchymal stem cells, hMSCs) had over 90% post-injection viability over 7 days and 6-37 folds proliferation, depending on the initial cell density, in 28 days. In addition, stem cells encapsulated in Alg/Col hydrogels are functional. For example, hMSCs-laden Alg/Col hydrogel incubated in osteogenic medium osteogenically differentiate and form a mineralized matrix.

Advantages

Due to the post-injection stability, the Alg/Col hydrogel does not dilute or leak to the neighboring tissues as opposed to pure collagen solution. In addition, Alg/Col hydrogel is advantageous over pure alginate hydrogel because it contains native collagen with optimal biocompatibility, cell-interactive ligands and bioresorbability.

Embodiments of this invention pertain to a method to make a uniform collagen and alginate mixed hydrogel. Two precursor solutions can be stored at low temperature (0.5-8° C.) for a long time (minimum 3 months). Long-term storage eases manufacturing and product distribution. Due to a low concentration (1 to 10 mg/mL) of $CaSO_4$ in the collagen precursor solution, the mixing process is relatively easy and there is no need to use a special mixing tool (such as for example a luer-lock or connector syringes). Dry collagen fibers could be added to the hydrogel to make a composite and obtain the desired mechanical properties of the hydrogel in light of the objective of the invention. In addition, crosslinkers (e.g. multi-arm polyethylene glycol succinimidyl carboxymethyl ester) could be added to alginate precursor to tune the mechanical properties and/or degradation kinetics of the hydrogel. Two precursor solutions of Alg/Col hydrogel can be stored, mixed with patient's cells, and used in the operation room.

In one example the invention is a delivery platform for cells or therapeutics. The delivery platform has (1) an alginate precursor solution, wherein alginate is dissolved in a calcium free and basic pH medium, and (2) a collagen and $CaSO_4$ precursor solution, wherein collagen is dissolved in a calcium free and acidic medium supplemented with $CaSO_4$ to make a collagen precursor solution. The calcium free and basic pH medium is defined as a pH higher than physiological pH (7.4). The calcium free and acidic medium is defined as a pH lower than physiological pH (7.4). The supplemented CaSO4 is in the range of 1-10 mg/mL.

In another example, the invention is a method of delivering cells or therapeutics. For this method, one would have (1) an alginate precursor solution, where alginate is dissolved in a calcium free and basic pH medium, and (2) a collagen and $CaSO_4$ precursor solution, wherein collagen is dissolved in a calcium free and acidic medium supplemented with $CaSO_4$ to make a collagen precursor solution. The calcium free and basic pH medium is defined as a pH higher than physiological pH (7.4). The calcium free and acidic medium is defined as a pH lower than physiological pH (7.4). The supplemented CaSO4 is in the range of 1-10 mg/mL.

In a further example for the delivery platform and the method, the alginate precursor solution and the collagen and CaSO4 precursor solution are stored at a temperature ranging from 0.5° C. to 8° C.

In yet a further example of the delivery platform and the method, the alginate precursor solution and the collagen and CaSO4 precursor solution have been mixed together after the cells and/or the therapeutics have been added to the collagen and CaSO4 precursor solution or to the alginate precursor solution.

In still a further example of the delivery platform and the method, the alginate precursor solution and the collagen and CaSO4 precursor solution have been mixed together where the alginate to the collagen weight ratio in the mixed platform ranges from 1/10 to 10/1.

BRIEF DESCRIPTION OF THE DRAWINGS

(FIG. 2D) evolution of storage modulus with time at 37° C. for Alg/Col 1/0.5 hydrogel with 0 (blue 210), 5 (brown 230), 10 (red 240), and 15 (green 220) mg/mL $CaSO_4$ concentration (FIG. 2E) effect of $CaSO_4$ concentration on the storage modulus of Alg/Col 1/0.5 hydrogel after 900 seconds at 37° C. Error bars in FIG. 2C and FIG. 2E correspond to means±1 SD for n=3. FIG. 2F shows the effect of precursor solutions storage time on the shear dependent viscosity of the alg/col 1/0.5 hydrogel. The collagen and alginate precursor solutions were stored at 4 °C. for 0 days (red), 7 days (blue), 14 days (green), or 28 days (brown) and mixed right before the viscosity measurement. Error bars in 2c and 2e correspond to means ±1 SD for n=3.

(FIG. 3G) release kinetics of BSA from Alg/Col 1/0.25 (green), Alg/Col 1/0.5 (red), and Alg/Col 1/1 (blue) hydrogels. (FIG. 3H) release kinetics of BMP2 from alg/col 1/0.25 (green), alg/col 1/0.5 (red), and alg/col 1/1 (blue) hydrogels. Error bars in FIG. 3F-3H correspond to means±1 SD for n=3. 310=green, 320=red, and 330=blue.

FIGS. 4A-F show according to an exemplary embodiment of the invention live ('green') and dead ('orange') hMSCs encapsulated in Alg/Col 1/0.5 hydrogel with 0.5 million cells/mL (FIG. 4A), 1 million cells/mL (FIG. 4B) and 5 million cells/mL (FIG. 4C) cell densities 24 hr after encapsulation. (FIG. 4D) effect of alginate to collagen weight ratio on the viability of hMSCs encapsulated in Alg/Col hydrogel with 1 million cells/mL density 24 hr after encapsulation, (FIG. 4E, green (0.5 mg), red (1 mg), blue (1.5 mg) is order from left to right of the bars) effect of $CaSO_4$ concentration in Alg/Col 1/0.5 hydrogels on the viability of encapsulated hMSCs, (FIG. 4F) DNA content of hMSC-laden Alg/Col 1/0.5 hydrogels with cell densities of 0.5, 1 and 5 million cells/mL incubated in basal medium over 28 days. Scale bars in 4a-c are 100 μm. Error bars correspond to means±1 SD for n=3.

(FIG. 6A) 3D images of new bone formation in calvarial defect site without hydrogel injection (Blank) or with injection of alg/col 1/0.5 hydrogel alone (Gel) or BMP2-loaded alg/col 1/0.5 hydrogel (Gel+BMP2) after 4 weeks or 8 weeks. (FIG. 6B, blue is blank, green is gel, and gel+BMP2 is red which is the order of the bars from left to right) Quantitative bone volume fraction (BV/TV) in calvarial defect site. Data are shown as mean±SD (n=6 per time point per group).

FIGS. 8A-C show according to an exemplary embodiment of the inventionresults of immunohistochemical staining of osteocalcin (OCN) or osteopontin (OPN) at the newly regenerated tissue in calvarial defect site. (FIG. 8A) OCN and OPN staining images at the defect sites without hydrogel injection (Blank) or with injection of Alg/Col 1/0.5 hydrogel alone (Gel) or BMP2-loaded Alg/Col 1/0.5 hydrogel (Gel+BMP2) after 4 weeks or 8 weeks. (FIGS. 8B-C, blue is blank, green is gel, and gel+BMP2 is red which is the order of the bars from left to right) Quantitative percentages of OCN or OPN positive area in calvarial defect site. Data are shown as mean±SD (n=6 per time point per group).

DETAILED DESCRIPTION

This invention describes a delivery platform for cells or therapeutics, compositions for a delivery platform for cells or therapeutics, a method of using delivery platform and/or compositions for cells or therapeutics, and a facile method to make injectable collagen/alginate/CaSO$_4$ hydrogels. The inventors investigated the effect of alginate to collagen weight ratio and CaSO$_4$ content on shear-thinning properties, injectability, and storage modulus of the hydrogels. In addition, the inventors studied the hydrogels microstructure, distribution of alginate and collagen within the hydrogel, and release kinetics of a model protein from the hydrogels. Furthermore, the inventors evaluated the viability, proliferation, and osteogenic differentiation of hMSCs in hydrogels. All of which are reported and discussed herein.

Collagen solution is an injectable liquid that crosslinks at 37° C. and physiological pH and loses its injectability following crosslinking. A potential dilution with body fluid, leakage to neighboring tissues and a chance of being washed away before gelation limit the use of uncrosslinked collagen solution for cell and/or protein delivery in regenerative medicine. In addition, a low viscosity and inferior structural stability of collagen precursor solution, limits its application as bioink in 3D bioprinting. The inventors discovered and described herein a facile method to improve the viscosity, post-injection stability and mechanical properties of injectable collagen matrix via incorporating alginate and CaSO$_4$ into the matrix.

The Alg/Col hydrogel preparation involved an alginate precursor solution and a collagen/CaSO$_4$ precursor solution. The two precursor solutions could be stored at 4° C. (or at a range of 0.5° C. to 8° C.) and pipette mixed before use, as opposed to previously reported methods to make collagen/alginate-based hydrogels that necessitated using a post-injection crosslinking in CaCl$_2$ solution, a collagen pre-processing step and/or special instruments such as coaxial nozzles and luer-lock syringes.

Evenly distributed alginate and collagen in the Alg/Col matrix (see FIG. 3E) confirmed a uniform mixing of collagen and alginate precursor solutions. Since the calcium ions were present in the collagen precursor solution before mixing, a uniform mixing of two solutions indicated an even distribution of alginate crosslink density in the Alg/Col hydrogels.

The storage modulus and viscosity of alginate hydrogels at 4° C. (see FIG. 2A and initial values in FIGS. 2B and 2D) increased with incorporation of collagen into the hydrogel and increasing the collagen concentration. Since collagen is not crosslinked at 4° C. (or at a range of 0.5° C. to 8° C.) the higher storage modulus and viscosity of alginate hydrogel in the presence of collagen might be due to an interaction between collagen and alginate and/or collagen and calcium ions.

Figure 2A:
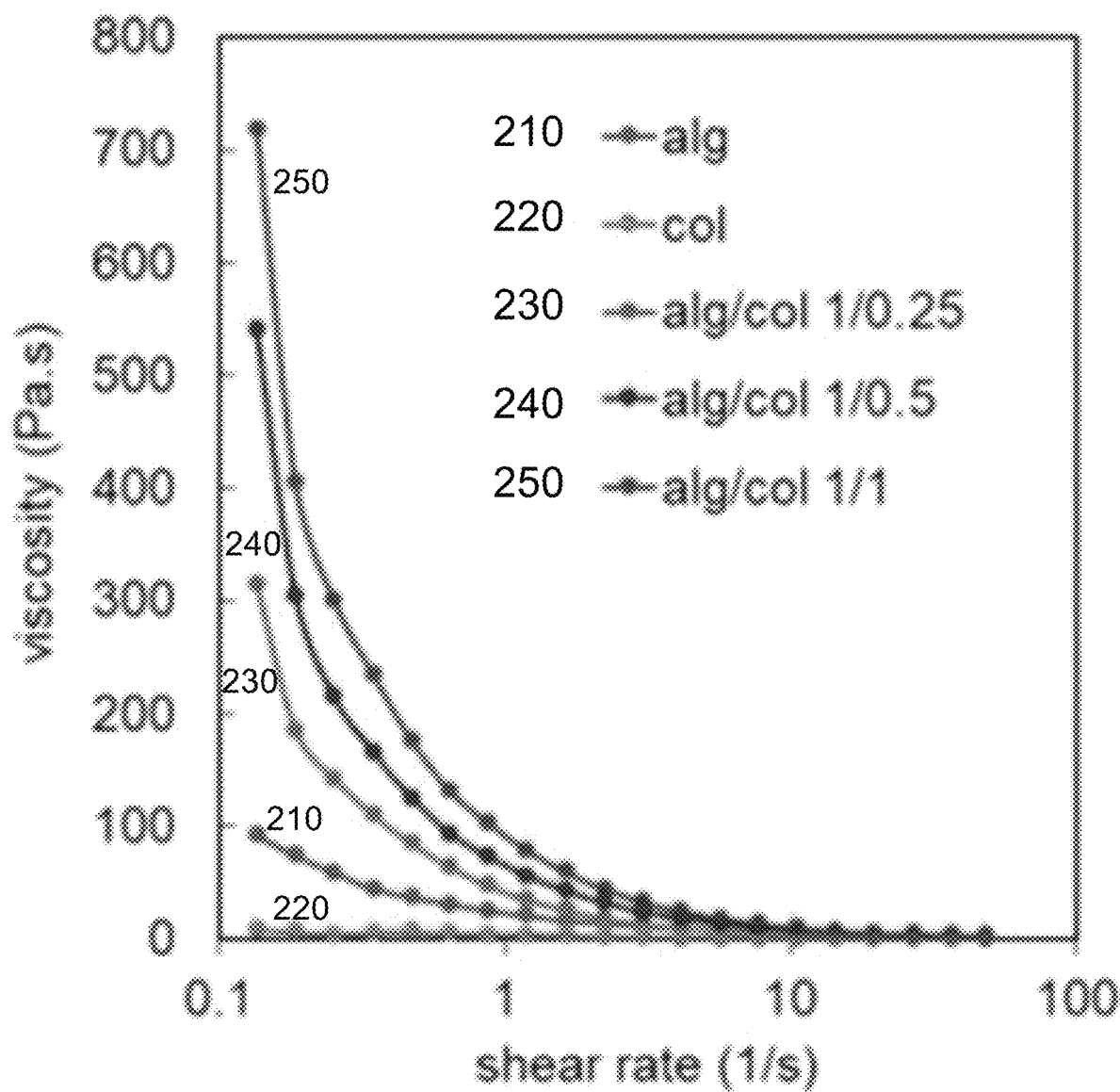
FIGS. 2A-F show according to an exemplary embodiment of the invention (FIG. 2A) the effect of shear rate on the viscosity of alginate (alg, blue line 210), collagen (col, green line 220), alg/col 1/0.25 (brown line 230), alg/col 1/0.5 (red line 240), and alg/col 1/1 (purple line 250) hydrogels, (FIG. 2B) evolution of storage modulus with time at 37° C. for alginate gel (blue 210), collagen (green 220), alg/col 1/0.25 (brown 230), alg/col 1/0.5 (red 240), and alg/col 1/1 (purple 250) hydrogels with 1 mg/mL $CaSO_4$ concentration (FIG. 2C) effect of alginate to collagen weight ratio on the storage modulus of Alg/Col gels after 900 seconds at 37° C.
Figure 2B:
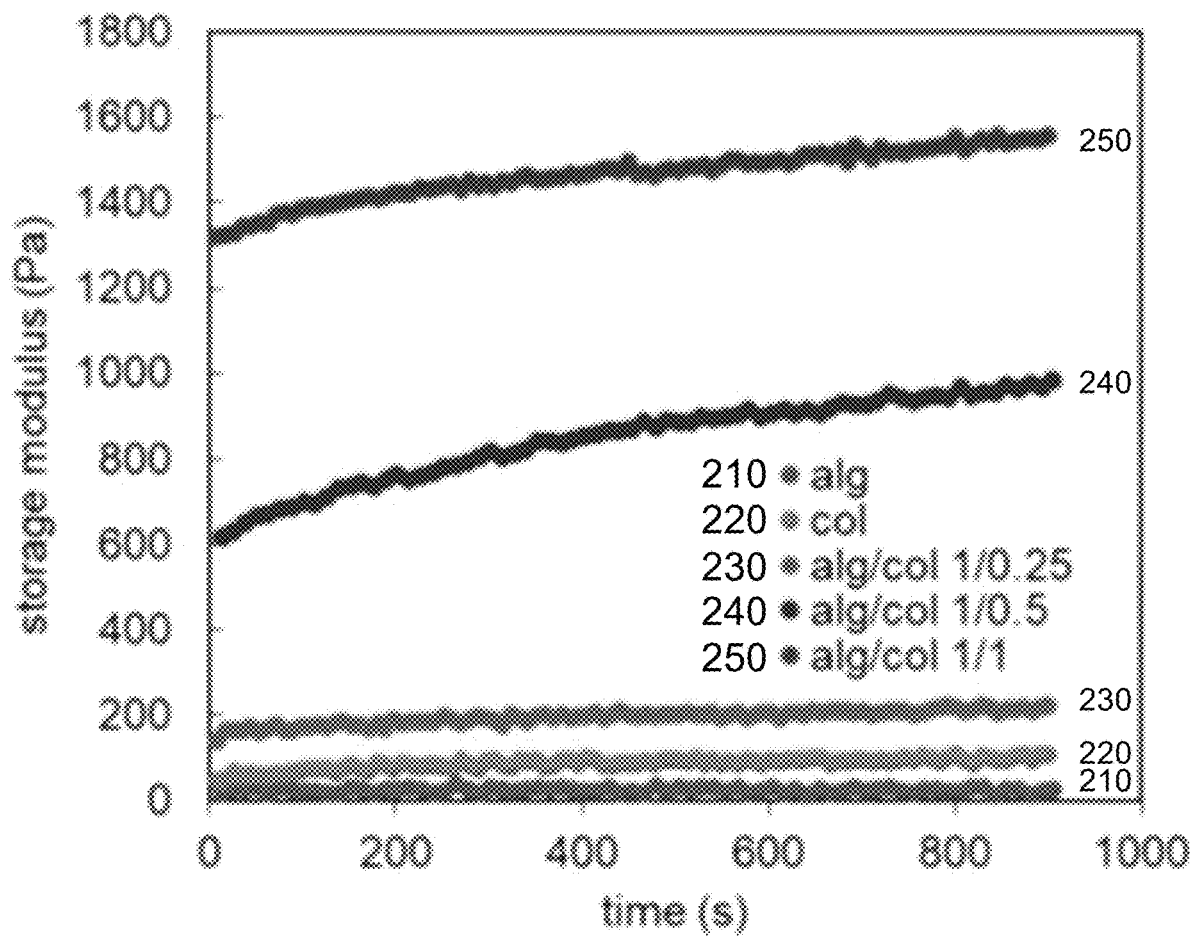
Figure 2C:
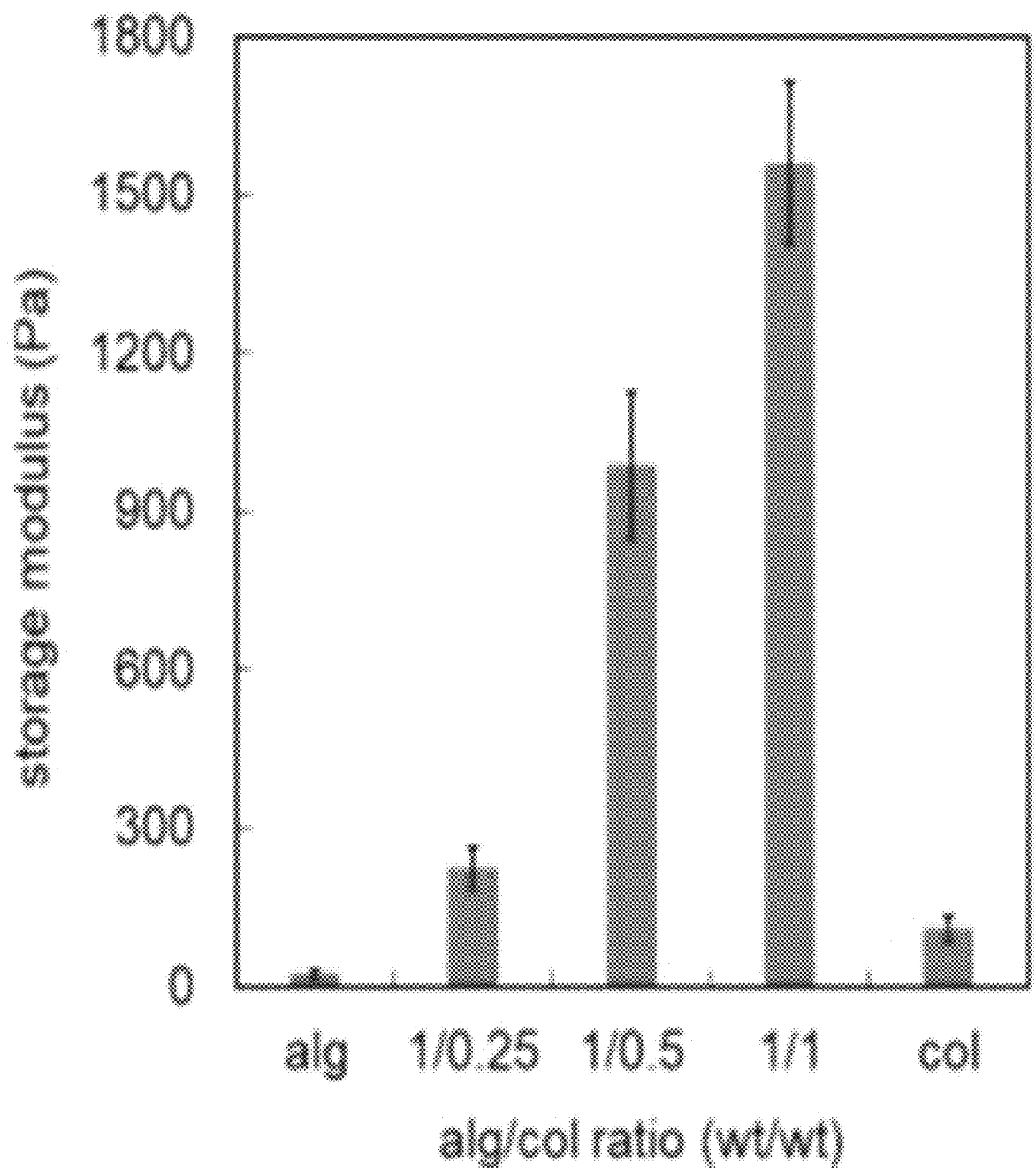

According to the results, as discussed infra, the storage modulus of crosslinked pure alginate hydrogel did not alter when the temperature was changed from 4° C. to 37° C., as opposed to pure collagen hydrogel with a growth in the storage modulus (FIGS. 2A-E and See Results, infra). Therefore, a time dependent growth in the storage modulus of the Alg/Col hydrogels at 37° C. was attributed to the collagen crosslinking within a pre-crosslinked alginate matrix. Also, the storage modulus of fully crosslinked Alg/Col hydrogels was significantly higher than that of pure alginate hydrogel (FIG. 2C).

The storage modulus of pure collagen hydrogel (2.5 mg/mL) in this invention was 110 Pa. The storage modulus of pure collagen hydrogel is concentration dependent and increases with collagen concentration (ccol) with ccol$^{2.1}$ at 37° C. Therefore, the storage modulus of pure collagen hydrogel increases by 4.3 folds, when ccol doubles. Results of the inventors' studies showed when ccol in Alg/Col matrices doubled from 1.25 mg/mL (alg/col 1/0.25) to 2.5 mg/mL (alg/col 1/0.5), the storage modulus of the Alg/Col hydrogel increased by 4.4 folds. However, the storage modulus of Alg/Col hydrogels increased by only 1.6 folds when ccol doubled from 2.5 mg/mL (Alg/Col 1/0.5) to 5 mg/mL (Alg/Col 1/1). Further, while the final storage modulus of Alg/Col hydrogels increased, the rate of growth of storage modulus with time dropped with increasing the collagen concentration (FIGS. 2A-E and See Results, infra). A smaller rate of growth in storage modulus of alg/col 1/1 hydrogel with ccol, as well as a smaller rate of growth in the storage modulus of Alg/Col 1/1 hydrogel with time compared to those of Alg/Col 1/0.25, alg/col 1/0.5 hydrogels (FIGS. 2A-E and See Results, infra) indicated a more pronounced impact of alginate and CaSO$_4$ on collagen crosslinking at high ccol (5 mg/mL). A higher initial viscosity (FIG. 2A) might hinder the collagen macromolecular motion and crosslinking at high collagen concentrations.

An increase in the storage modulus of Alg/Col hydrogels with CaSO$_4$ concentration was due to a raise in the density of Ca$^{2+}$-driven crosslinking density of alginate. Also, an interaction between calcium ions and collagen might contribute to concentration-dependent increase in storage modulus of Alg/Col hydrogels with CaSO$_4$ concentration. It was shown that collagen molecules chelate calcium ions due to an electrostatic interaction between the negatively charged carboxyl groups on the collagen molecules and positively charged calcium ions and the elastic modulus of collagen fibrils increases with calcium ion concentration.

The viability of cells encapsulated in Alg/Col hydrogels was comparable with or higher than cell viability in alginate-based or collagen-based hydrogels reported elsewhere. For instance, the viability of placenta-derived MSCs in collagen hydrogels was over 90% after 24 hours of incubation. The viability of MSCs in RGD peptide-modified injectable alginate hydrogel was around 90%. MSC-loaded core-shell alginate/collagen fibrous hydrogels were made via injection of the precursor solutions through a concentric nozzle into a bath of CaCl$_2$. The viability of MSCs in the core-shell alginate/collagen hydrogel was around 70% after 7 days. Results based on this invention showed that the viability of hMSCs in injected Alg/Col hydrogels was over 90% during 7 days of incubation, regardless of the alginate to collagen ratio or CaSO4 concentration.

A continuous proliferation of MSCs in collagen-based matrices were previously reported. For example, the number of rat MSCs encapsulated in collagen hydrogel (10$^5$ cells/mL initial cell density) monotonically increased over 21 days with 3 folds growth from day 7 to 21. In contrast, the number of hMSCs encapsulated in RGD peptide-grafted alginate hydrogels (2-20×10$^6$ cells/mL initial cell density) did not grow in two weeks. Results basd on this invention showed the number of hMSCs in Alg/Col hydrogels during 28 days of incubation raised by 6.2-37.2 folds (1.3-2 folds increase from day 7 to 21) depending on the initial cell density (0.5-5×10$^6$ cells/mL). The DNA content of hMSCs in alg/col hydrogels reached a plateau corresponding to around 30 million cells/mL that could be interpreted as the highest cell density within alg/col hydrogels.

The inventors further showed that osteo-inductive conditions stimulated osteogenic differentiation of hMSCs in Alg/Col hydrogels at all studied cell densities (0.5, 1, 5 million cells/mL).

The Alg/Col hydrogel based on this invention was injectable through commercially available needles and the injected hydrogel was stable right after injection. The viscoelastic characteristics of Alg/Col hydrogel were tunable via changing the alginate to collagen ratio or CaSO$_4$ concentration. In addition, Alg/Col hydrogels supported high viability as well as proliferation and differentiation of encapsulated stem cells. Therefore, the alg/col hydrogel could potentially be used for delivery of cells/biomolecules in surgeries or as bioink in bioprinting applications.

Materials and Methods

Exemplary materials and methods are described as proof of concept of the invention, which should not be regarded as limiting to the invention.

Materials

Rat tail collagen type I was purchased from Corning Inc., Sodium alginate (alginate, 500GM) was purchased from Pfaltz & Bauer Inc. (Hayward, CA, USA). Sodium hydroxide (NaOH), ethanol, 5-(Aminomethyl)Fluorescein Hydrochloride, and Texas Red™-X, Succinimidyl Ester were purchased from Thermo Fisher Scientific. Calcium sulfate (CaSO$_4$), 2-(N-Morpholino)ethanesulfonic acid (MES), N-(3-Dimethylaminopropyl)-N'-ethylcarbodiimide hydrochloride (EDC), N-Hydroxysulfosuccinimide (NHS), dexamethasone, ascorbic acid and β-sodium glycerophosphate were received from Sigma-Aldrich (Hayward, CA, USA). Collagenase, Calcein AM/Ethidium homodimer-1 Live/Dead assay kit, and Quant-iT PicoGreen DNA assay kit were purchased from Thermo Fisher Scientific (Hayward, CA, USA). QuantiChrom alkaline phosphatase activity (ALP) kit and Calcium Assay kit were purchased from BioAssay Systems (Hayward, CA, USA).

Methods

Hydrogel Preparation

Figure 1:
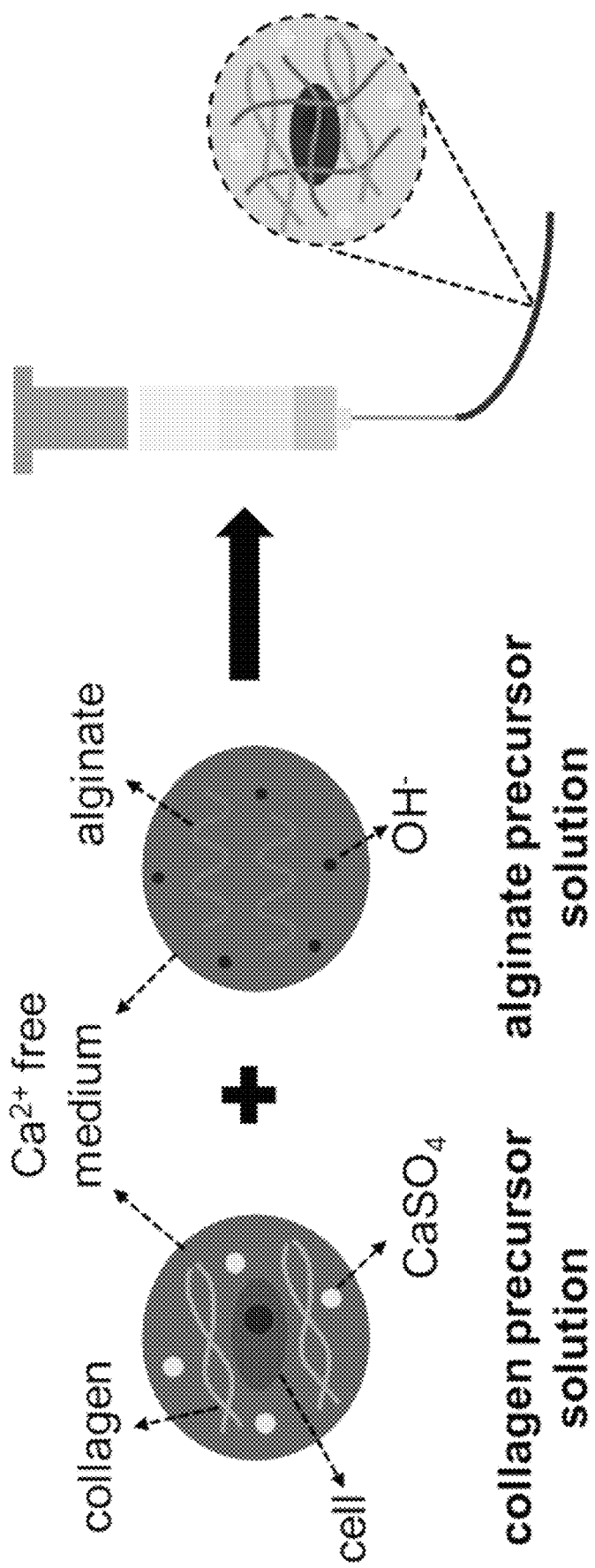
FIG. 1 shows according to an exemplary embodiment of the invention a schematic diagram for injectable Alg/Col hydrogel preparation. The alginate precursor solution was prepared by dissolving alginate in calcium-free DMEM medium and adjusting the pH using NaOH. The collagen precursor solution was prepared by adding collagen to calcium-free DMEM medium and then supplementing the collagen solution with $CaSO_4$. In an example, hMSCs were suspended in collagen precursor solution and then two precursor solutions were pipette mixed.

A schematic representation of the method used to prepare Alg/Col hydrogels is shown in FIG. 1. Alginate was dissolved in calcium free DMEM medium at 1% (w/v) concentration. solution was filtered using a 0.22 μm PES filter (Millex, Millipore Sigma) and supplemented with 1N NaOH at 4, 8, or 16 μL/mL to prepare alginate precursor solution for Alg/Col 1/0.25, Alg/Col 1/0.5 or Alg/Col 1/1 hydrogels, respectively. The alginate solution was sterilized by filtration using 0.22 μm Millex syringe filters and stored at 4° C. Calcium sulfate (CaSO$_4$) was sterilized using electron beam (E-beam) at a dose of 25 kGy, following ISO 11137-2:2006 standard. DI water was sterilized using a 0.22 μm PES filter. 1 mL Sterile DI water was then added to 100 mg sterile CaSO$_4$ and the suspension was vortexed for 5 minutes. 750, 500, or 0 μL calcium free DMEM medium was added to 250, 500 or 1000 μL of collagen (collagen I from rat tail, Corning Inc) at 4° C., for 1/0.25, Alg/Col 1/0.5 or Alg/Col 1/1 hydrogels, respectively. Then, the collagen solution was supplemented with 0, 10, 20, or 30 μL of vigorously vortexed CaSO$_4$ suspension (corresponding to 0, 0.5, 1, and 1.5 mg/mL CaSO$_4$ concentrations in the hydrogel) and mixed via pipetting to make collagen precursor solutions. The collagen precursor solution was added to the alginate solution at 1:1 volume ratio and pipetted multiple times. To make pure alginate hydrogel (Alg), alginate was dissolved in calcium free DMEM medium at 1% (w/v) concentration. 20 μL of vigorously vortexed CaSO$_4$ suspension (100 mg/mL) was suspended in 1 mL of calcium free DMEM medium. Then alginate solution and CaSO$_4$ suspension were mixed at 1:1 ratio. To make pure collagen hydrogel (Col), collagen was added to calcium free DMEM medium at 2.5 mg/mL concentration (corresponding to collagen concentration in Alg/Col 1/0.5 gel) and the pH was adjusted to 7.4 using sterile 1N NaOH.

Rheological Measurements and Injectability

The alg/Col hydrogels with different alginate/collagen weight ratios or CaSO$_4$ concentrations, were prepared at 4° C. and loaded on the Peltier plate of an ARES-G2 rheometer (TA Instruments, New Castle, DE). An 8 mm parallel plate stainless steel geometry was used at a gap distance of 200 μm. To test the shear thinning characteristics, the viscosity of the hydrogels at 4° C. was measured when the shear rate increased from 0.1 to 50 Hz. To test the temperature-responsive evolution of the storage modulus of the gels, the gels were equilibrated at 4° C. for 15 minutes on the Peltier plate, then the temperature of the Peltier plate was changed from 4° C. to 37° C., a sinusoidal shear strain with 1% strain and 1 Hz frequency was applied to the sample, and the storage modulus (G') of the samples was recorded with time. Injectability of the Alg/Col hydrogels was tested via loading the gel into a 1 mm syringe (Norm-Ject syringe, Air-Tite Products Co., Inc., Virginia Beach, VA) and manual injection of the gel through a 20 G needle (PrecisionGlide, Becton Dickinson, Franklin Lakes, NJ) onto wells of a 6-well plate. The injected strut was imaged using a Zeiss AxioObserver Z1 microscope.

SEM Imaging

The Alg/Col hydrogels samples were immersed in liquid nitrogen and freeze-dried. The freeze-dried samples were dipped in liquid nitrogen and cut using a surgical blade. The hydrogel samples were then coated with gold using a SPI sputter (SPI Supplier Division of Structure Prob, Inc., West Chester, PA) for 180 seconds and imaged using a Field Emission Scanning Electron Microscope (Zeiss Sigma, White Plains, NY) at an accelerating voltage of 5 keV.

Alginate and Collagen Staining

For alginate fluorescent labeling, 500 mg of alginate was dissolved in 50 mL IVIES buffer (100 mM) containing EDC (1 mg/mL) and NHS (1 mg/mL) and allowed to react for 30 min at room temperature to activate the carboxylic acid groups. 5 mg of 5-(Aminomethyl)Fluorescein dye was dissolved in 100 μL DMSO, mixed with the activated alginate solution and stirred for 2 hr at room temperature in dark. The solution of stained alginate (s-alg) was then dialyzed against DI water using a dialysis tube (Spectrum Laboratories, Rancho Dominguez, CA) with 6-8 kDa molecular weight cutoff for 3 days at ambient temperature.

To stain collagen, 1 mg of Texas Red™-X, Succinimidyl Ester dye was dissolved in 100 μL DMSO and then diluted in 5 mL PBS. 100 μL of Alg/Col hydrogel or pure collagen hydrogel was injected onto wells of a 24-well plate, incubated at 37° C. for 30 minutes, and was thoroughly washed with PBS five times. Then, the dye solution was added to the hydrogel samples and incubated at room temperature in dark for 2 hr. The hydrogel samples were then washed with PBS five times (each time 30 min incubation at room temperature in dark) to fully remove the unreacted dye. The stained Alg/Col hydrogels were imaged using a Zeiss AxioObserver Z1 fluorescent microscope.

Protein Release

Bovine serum albumin (BSA, 1% w/v) was dissolved in Alg/Col 1/0.25, Alg/Col 1/0.5 and Alg/Col 1/1 hydrogels. 200 μL of the BSA loaded hydrogels or hydrogels without encapsulated BSA (control groups) was injected onto wells of a 24-well plate and incubated at 37° C. for 30 minutes. Then, 2 mL PBS was added to each well and the plate was incubated at 37° C. for 14 days. At each time point, the release medium was removed from the plates and replaced with fresh PBS. The removed release medium was transferred to siliconized microcentrifuge tubes and stored in a −80° C. freezer. After collecting the release media at all time points, the total protein content was measured with BCA Protein Assay Kit (Thermo Fisher Scientific) according to manufacturer's instructions. The normalized released protein at each time point was calculated by subtracting the protein released from BSA-laden samples from that of the control samples. The BSA release tests were done in triplicate.

hMSCs Culture

Human Mesenchymal Stem Cells (hMSCs) were cultured in DMEM medium (Life Technologies, USA) supplemented with 10% fetal bovine serum (FBS, Life Technologies, USA) and 1% Penicillin and Streptomycin (hereafter referred to as basal medium) at 37° C. in a 5% CO2 humidified incubator. After reaching 70% confluency, hMSCs were enzymatically lifted with trypsin-EDTA and used for in-vitro studies. All cells were passaged<6 times prior to the in-vitro studies.

Viability and Proliferation of hMSCs in Alg/Col Hydrogels

For cell encapsulation, 0.5, 1 or 5 million hMSCs were suspended in 500 μL collagen precursor solutions with different Alg/Col ratios or CaSO4 content. The collagen precursor solution was then added to 500 μL of sterile alginate solution and mixed gently via pipetting. 50 μL of the hMSC-laden hydrogel was injected onto wells of a 24-well plate and incubated at 37° C. for 30 minutes. The hydrogels were then incubated in 1 mL of basal medium at 37° C. and 5% CO2. For cell viability measurement, gels were stained with Calcein AM (2 μM) and Ethidium homodimer-1(4 μM) to image live and dead hMSCs according to manufacturer's to instructions and imaged using a Zeiss AxioObserver Z1 fluorescent microscope. The live/dead images were divided into smaller squares and the number of live and dead cells were counted manually to calculate the cell viability. To quantify the DNA content of the cell encapsulated hydrogel sample, at each time point, the samples were transferred into new wells and incubated in 500 μL of DMEM medium supplemented with collagenase (1 mg/mL) for 1 hour at 37° C. Then, 250 μL of 3% triton solution in PBS was added to each well and the attached cells were scrapped from the surface using a CytoOne cell scraper (USA Scientific Inc, Ocala, FL). Then the cell suspension was transferred to a microcentrifuge tube and sonicated to rupture the cell membrane. The lysate was centrifuged at 2000×g for 15 min at 4° C. and the supernatant was collected. The content of double-stranded DNA in the supernatant was measured using Quant-iT PicoGreen DNA assay according to manufacturer's instructions.

Osteogenic Differentiation of hMSCs in Alg/Col Hydrogels

For osteogenic differentiation, 50 μL of hMSC-laden alg/col hydrogel with 0.5, 1 or 5 million cells/mL cell number was injected onto wells of a 24-well plate and incubated in 1 mL of basal medium at 37° C. and 5% CO2. After 24 hr, the medium was replaced with osteogenic medium (basal medium supplemented with 100 nM dexamethasone, 50 μg/mL ascorbic acid, 10 mM β-sodium glycerophosphate) or fresh basal medium (control groups) and incubated for 28 days. To measure ALP activity, at each time point (0, 7, 14, 21, and 28 days), hydrogel samples were transferred into new wells and incubated in 500 μL of DMEM medium supplemented with collagenase (1 mg/mL) for 1 hour at 37° C. to digest the gels. Then, 250 μL of 3% triton solution in PBS was added to each well and the attached cells were scrapped from the surface using a cell scraper. Then the cell suspension was transferred to a microcentrifuge tube and sonicated. The lysate was centrifuged at 2000×g for 15 min at 4° C. and the supernatant was collected. The ALP activity in the supernatant was measured using QuantiChrom ALP assay kit according to the manufacturer's Instructions, on the plate reader at 405 nm. To measure the calcium content, hMSC-laden hydrogel samples were first lysed as described supra. Then, 250 μL of 1N HCL solution was added to the lysate and mixed overnight at 4° C. Next, the lysate was centrifuged at 2000×g for 15 min at 4° C. and the supernatant was collected. The calcium content in the supernatant was measured using QuantiChrom Calcium assay kit according to the manufacturer's Instructions, on the plate reader at 612 nm. The ALP activity and calcium content at each time point were normalized by dividing by the DNA content at that time point. To visualize the mineralization, at day 28, the hMSC-laden gels were washed 3 times with PBS, stained with Alizarin red and imaged using a Zeiss AxioObserver Z1 microscope.

Statistical Analysis

All experiments were done in triplicate. Statistically significant differences between groups were tested using a two-way ANOVA with replication, followed by a two-tailed Students t-test. A p-value smaller than 0.05 ($p<0.05$) was considered statistically significant.

Results

The effect of shear rate on the viscosity of alginate (Alg, blue line 210), collagen (Col, green line 220), Alg/Col 1/0.25 (brown line 230), Alg/Col 1/0.5 (red line 240), and Alg/Col 1/1 (purple line 250) hydrogels is shown in FIG. 2A. At the minimum shear rate, the viscosities of Alg/Col hydrogels were significantly higher than that of alginate or collagen. The viscosity of Alg/Col hydrogels at minimum shear rate increased by 3.4, 5.9 and 7.9 folds when the collagen to alginate weight ratio increased from 0 to 0.25, 0.5, and 1, respectively. The viscosities of all hydrogels decreased when the shear rate increased from 0.13 to 48 (1/s). The shear-thinning characteristics indicated injectability of Alg/Col hydrogels regardless of the alginate to collagen ratio.

The effect of alginate to collagen weight ratio on the evolution of storage modulus of the Alg/Col hydrogels with time at 37° C. is shown in FIG. 2B. The storage modulus of alginate gel (blue markers 210) did not significantly change but the storage modulus of collagen (green markers 220)

increased by 2.1 folds over 900 seconds at 37° C. The storage modulus of Alg/Col 1/0.25 (brown markers 230), Alg/Col 1/0.5 (red markers 240), and Alg/Col 1/1 (purple markers 250) gels raised by 1.6, 1.6, and 1.2 folds, respectively after 900 seconds at 37° C. The storage moduli of Alg/Col hydrogels were significantly higher than those of alginate gel or collagen over 900 s. The storage modulus of Alg/Col gels after 900 seconds (FIG. 2C) increased from 23 Pa to 224 Pa, 985 Pa, and 1560 Pa with increasing the collagen to alginate weight ratio from 0 to 0.25, 0.5, and 1.

Figure 2D:
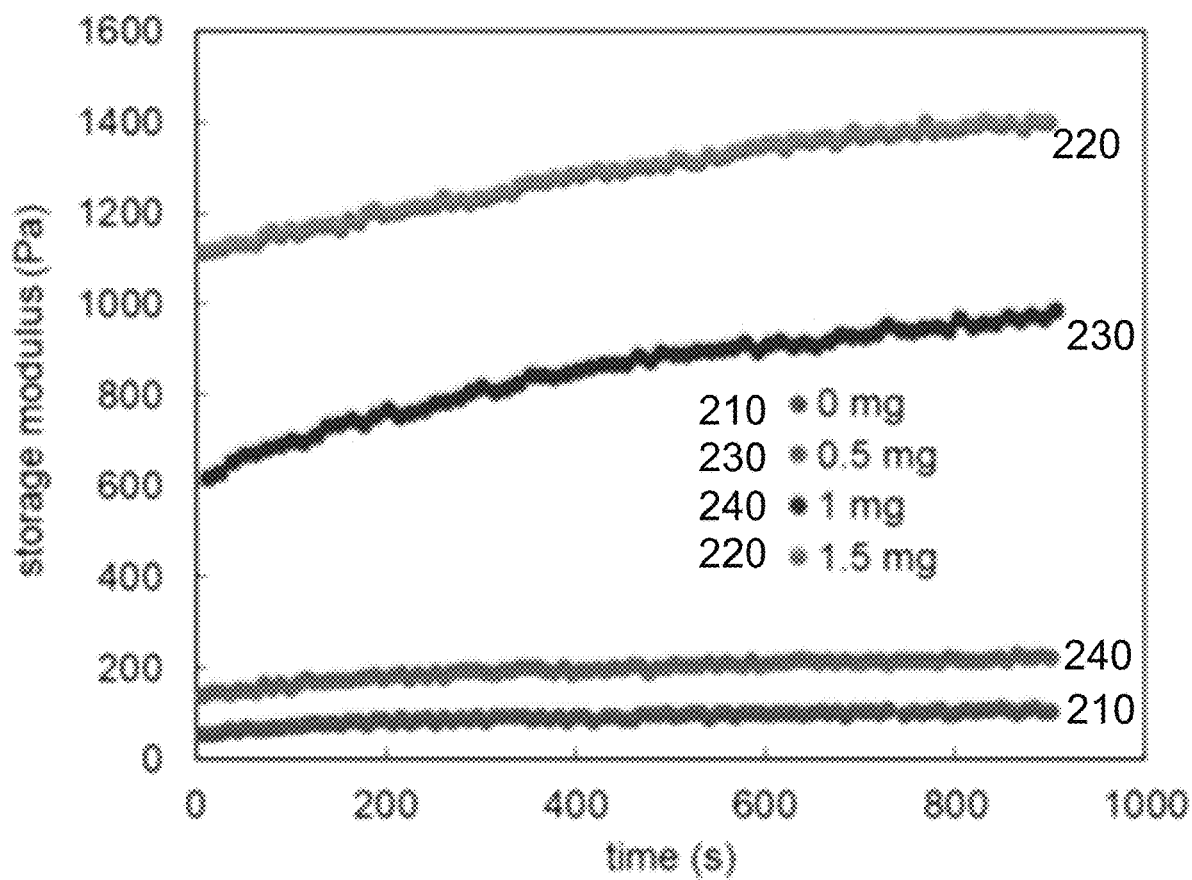
Figure 2E:
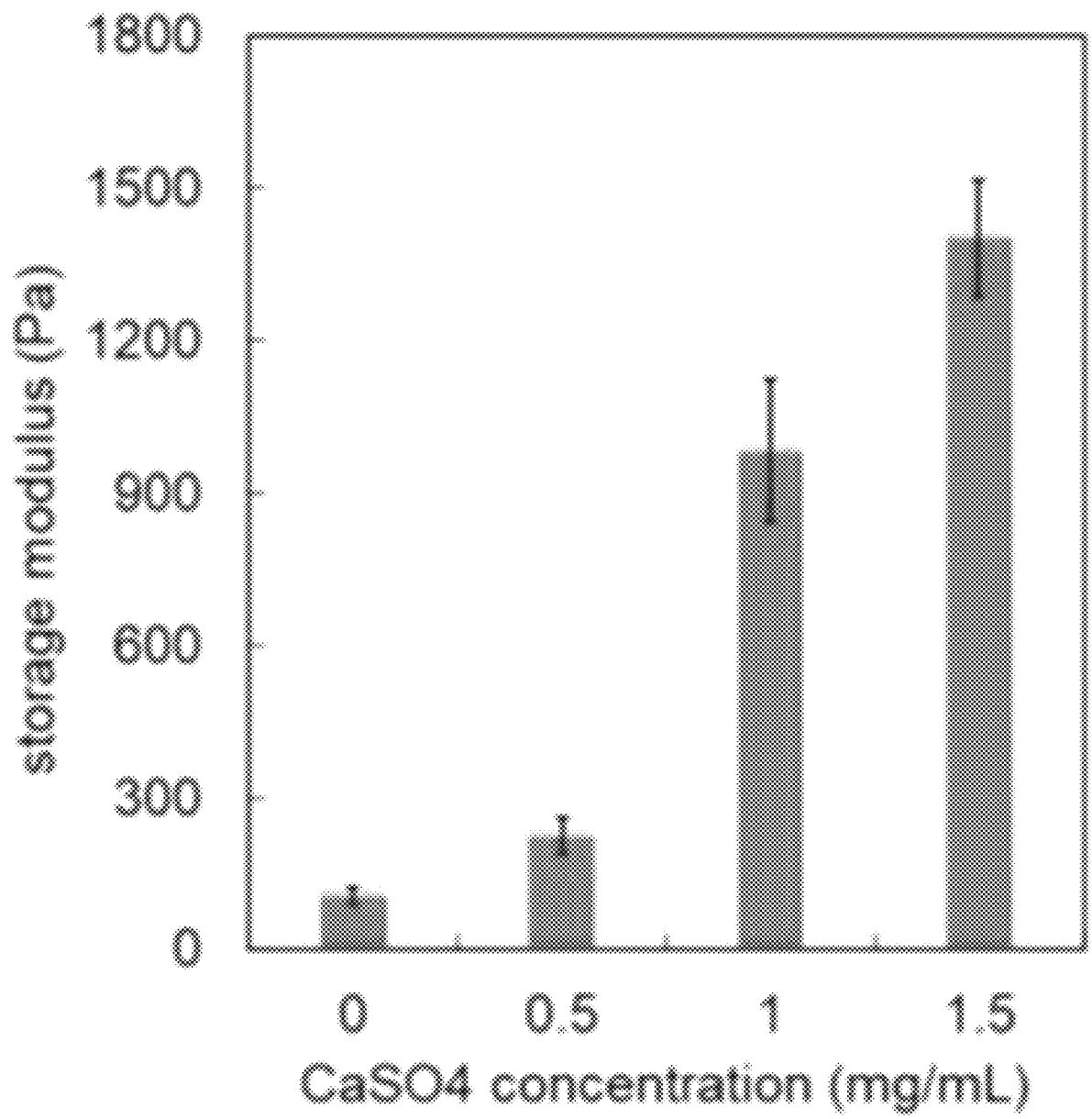
Figure 2F:
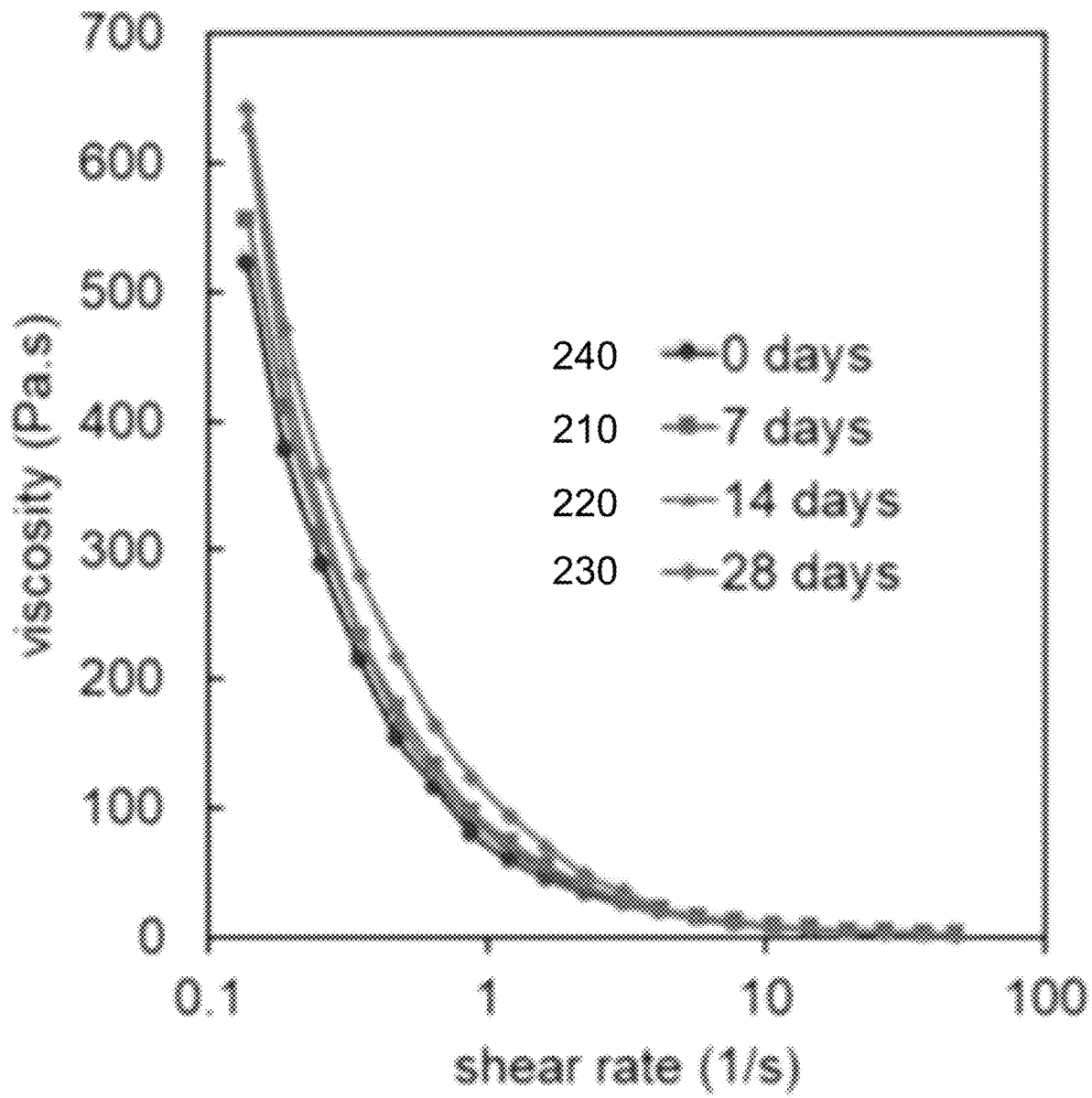

The effect of $CaSO_4$ concentration on the growth of storage modulus of Alg/Col 1/0.5 hydrogels at 37° C. is shown in FIG. 2D. The storage modulus of Alg/Col 1/0.5 gels increased by 1.8, 1.6, 1.6 or 1.3 folds over 900 seconds at 37° C. when the CaSO4 concentration was 0, 5, 10, or 15 (mg/mL), respectively. The storage modulus of Alg/Col 1/0.5 hydrogel at any time significantly increased with increasing the $CaSO_4$ concentration. For instance, after 900 seconds, the storage modulus of Alg/Col 1/0.5 hydrogel (FIG. 2E) increased from 105 to 223, 984, and 1402 with changing the CaSO4 concentration from 0 to 5, 10, and 15 (mg/mL).

Figure 3A:
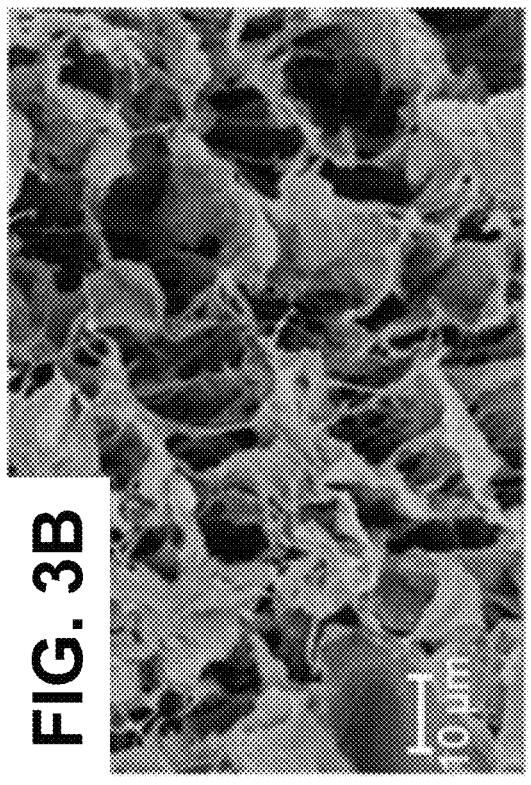
FIGS. 3A-H show according to an exemplary embodiment of the invention (FIG. 3A) Alg/Col 1/0.5 gel strut injected from a 20 G needle (FIG. 3B) A representative SEM image of Alg/Col 1/0.5 hydrogel (FIG. 3C) fluorescent image of Alg/Col alg (without collagen) prepared with green fluorescent-labeled alginate (FIG. 3D) fluorescent image of col hydrogel (without alginate) stained with red fluorescent dye (FIG. 3E) fluorescent image of Alg/Col 1/0.5 hydrogel that was prepared with green fluorescent-labeled alginate and then stained with red fluorescent dye to visualize collagen (FIG. 3F) degradation kinetics of alg/col 1/0.25 (green), alg/col 1/0.5 (red), and alg/col 1/1 (blue) hydrogels in PBS supplemented with collagenase and sodium citrate at 37° C.
Figure 3B:
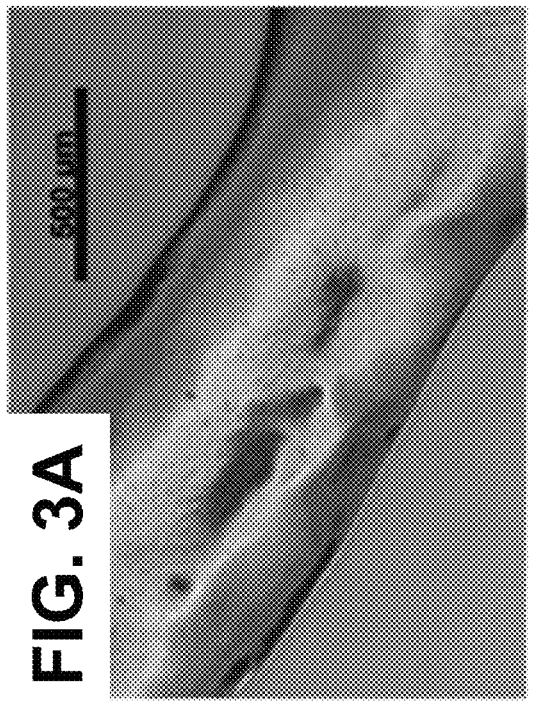

In addition to rheological characterization, the injectability of the Alg/Col hydrogels was also tested via manual injection of the gels through a 20 G. FIG. 3A shows an Alg/Col 1/0.5 gel strut injected from a 20 G needle. The average strut thickness was 810 μm which was slightly higher than the nominal inner diameter of a 20 G needle (600 μm). The alginate to collagen weight ratio and the concentration of $CaSO_4$ did not significantly impact the injectability of the gel or the injected strut thickness (data not shown). A representative SEM image of Alg/Col 1/0.5 hydrogel is shown in FIG. 3B. The hydrogel samples had a porous microstructure with average pore size of 15 μm.

Figure 3C:
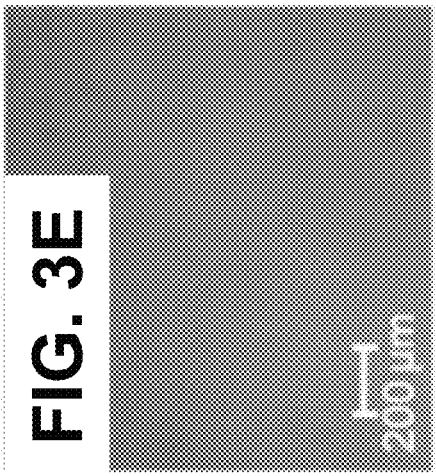
Figure 3D:
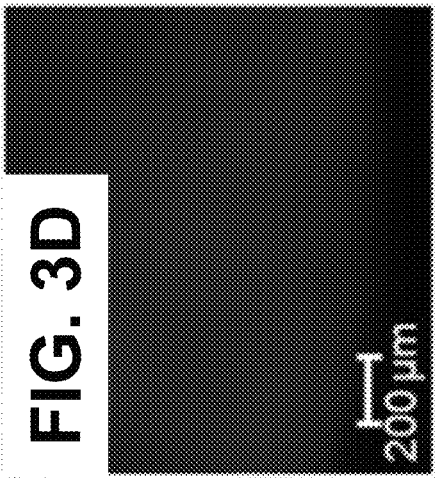
Figure 3E:
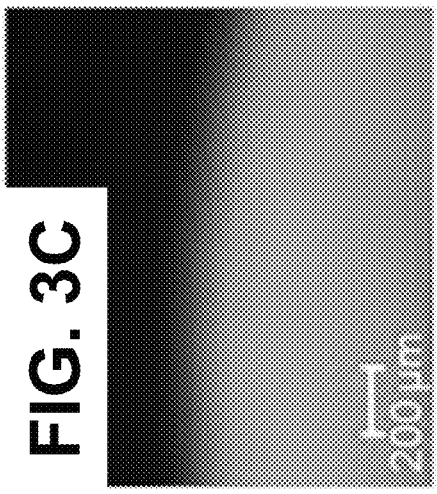

The distribution of alginate and collagen in Alg/Col hydrogels was evaluated via staining. FIG. 3C shows a fluorescent image of Alg hydrogel (without collagen) that was prepared with green fluorescent-labeled alginate (s-alg). The alginate in the absence of collagen was evenly distributed in the hydrogel indicated by a uniform green color (in FIG. 3C. A fluorescent image of col hydrogel (without alginate) stained with red fluorescent dye is shown in FIG. 3D. The collagen in the absence of alginate was evenly dispersed in the hydrogel. FIG. 3E shows a fluorescent image of Alg/Col 1/0.5 hydrogel that was prepared with green fluorescent-labeled alginate and then stained with red fluorescent dye to visualize collagen. The orange color indicated that both alginate hydrogel and collagen hydrogel contributed to the network and alginate gelation did not negatively impact the collagen network formation. Further, a uniform orange color in FIG. 3E showed that alginate and collagen were distributed evenly throughout the Alg/Col matrix without macrophase separation.

Figure 3F:
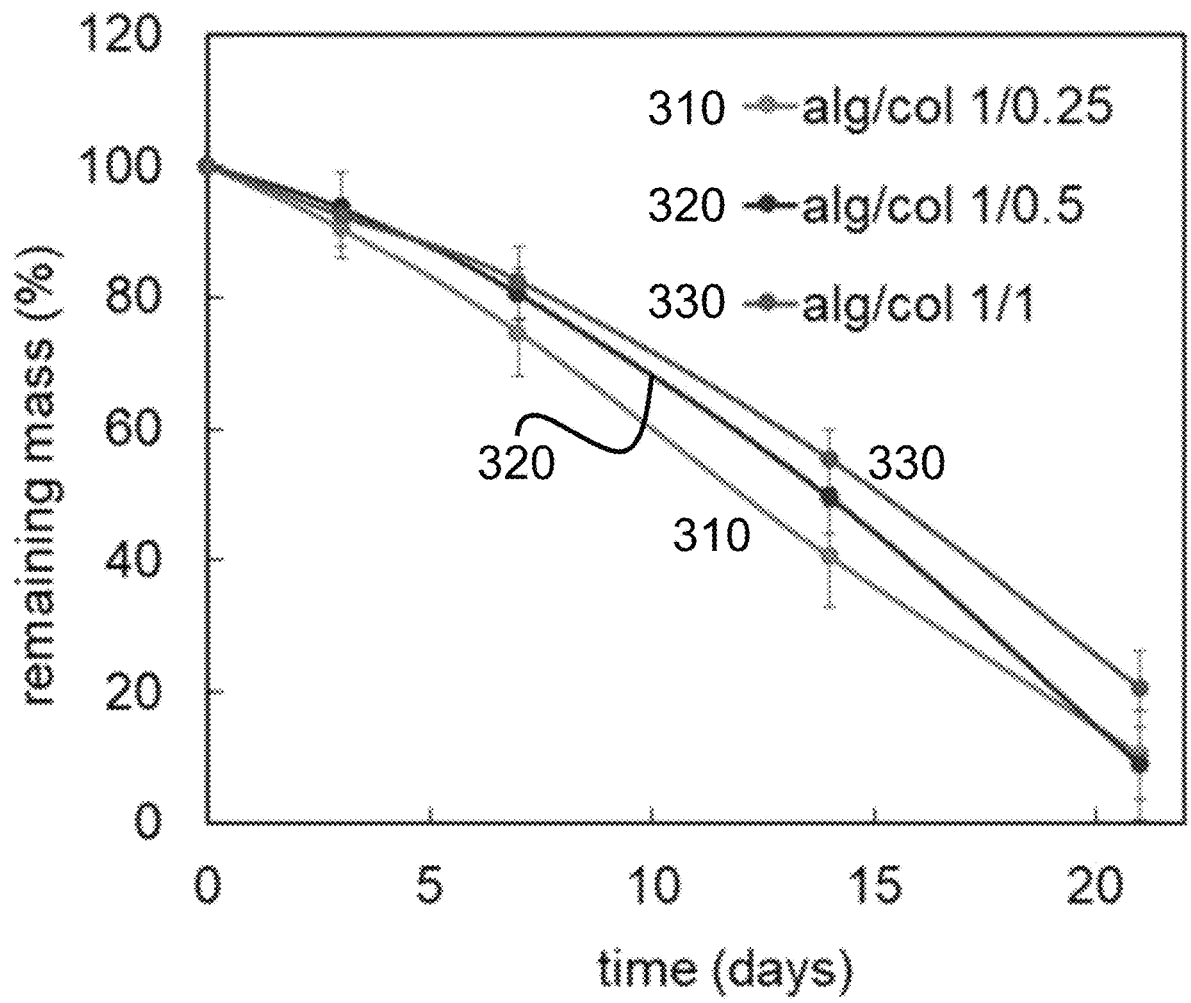

The degradation kinetics of alg/col hydrogels over 21 days at 37° C. in PBS supplemented with collagenase and sodium citrate is shown in FIG. 3F. The remaining mass of alg/col 1/0.25, alg/col 1/0.5, and alg/col 1/1 hydrogels monotonically decreased from 100% at day 0 to 10.5%, 9.0%, and 20.5% at day 21, respectively. The remaining mass of alg/col 1/1 was significantly higher than that of alg/col 1/0.25 hydrogel after 14 or 21 days.

Figure 3G:
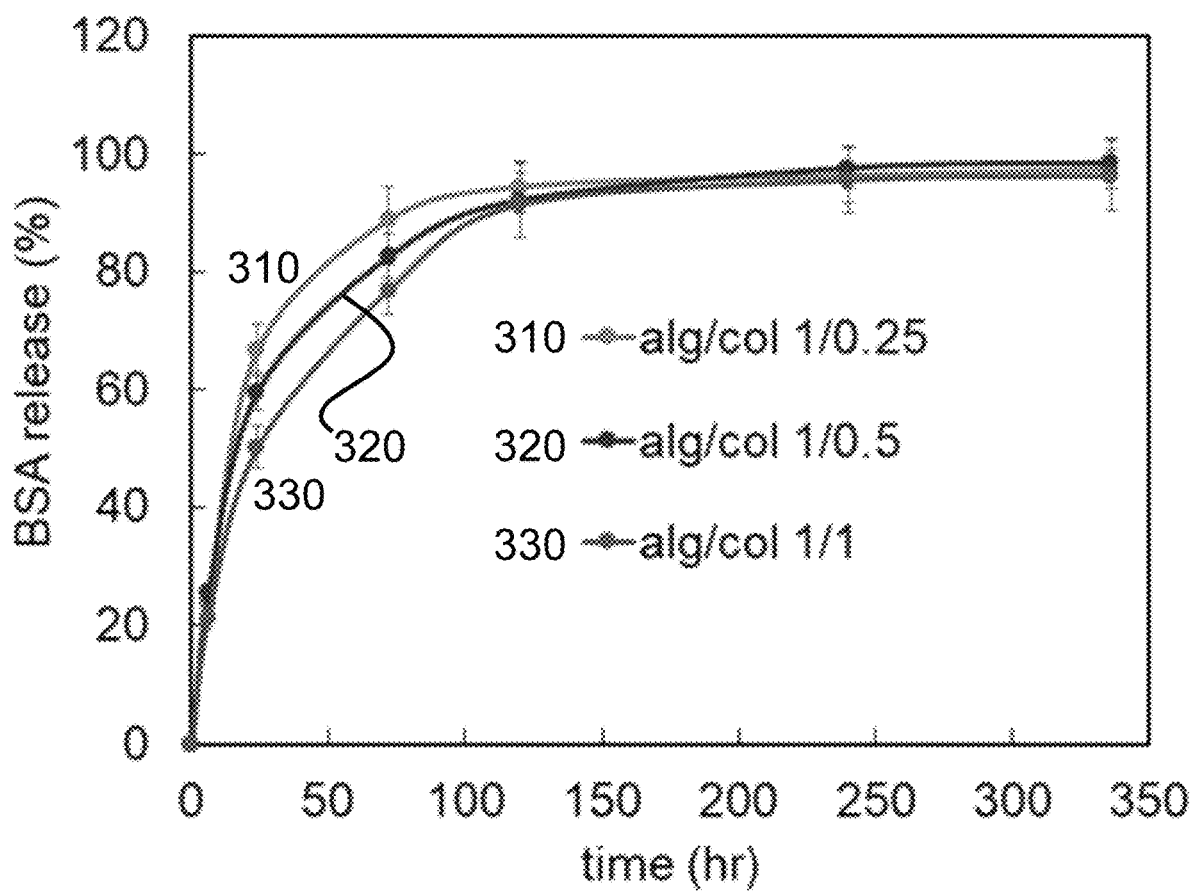
Figure 3H:
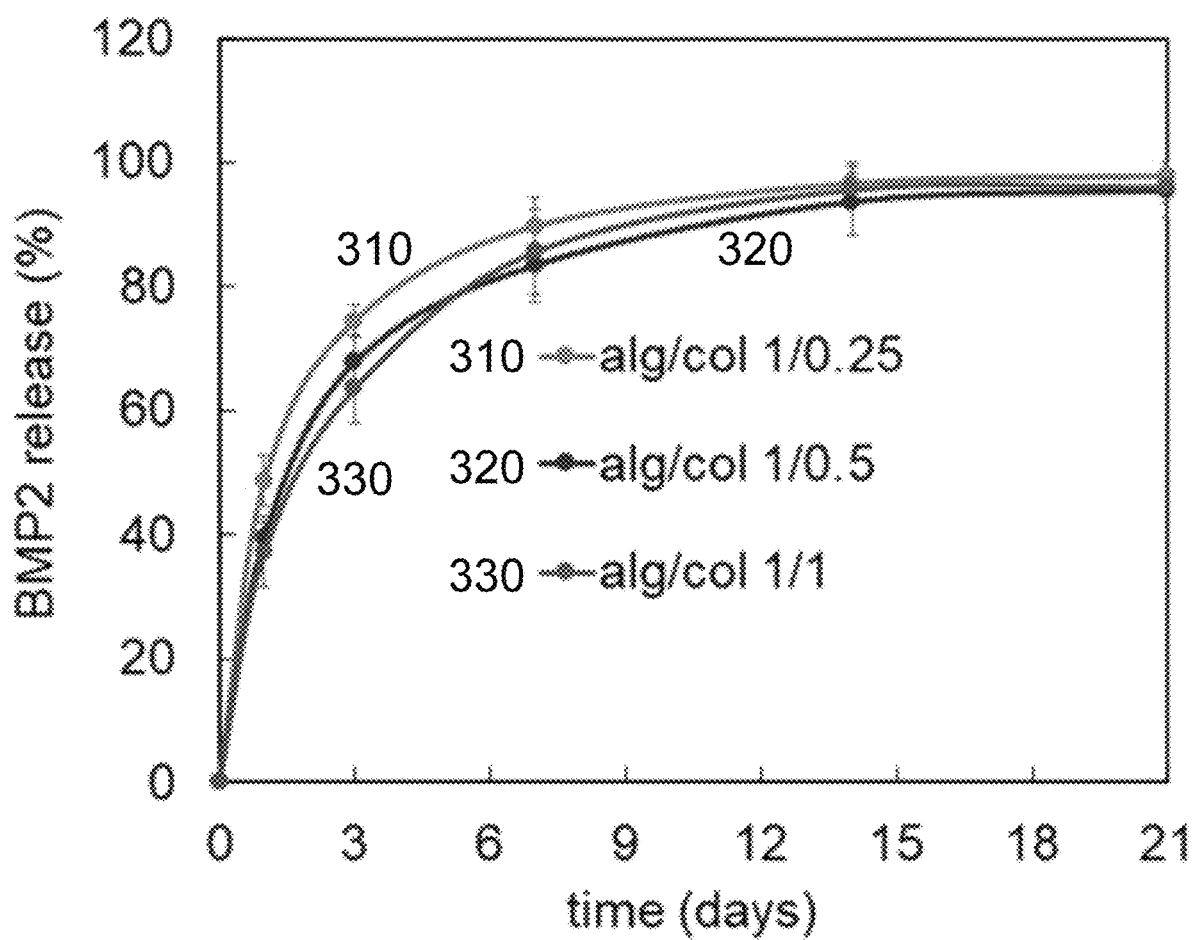

The release kinetics of BSA from alg/col hydrogels is shown in FIG. 3G. Following an initial burst release in the first day, the BSA release was slower from day 1 to 5 and reached a plateau after day 5. The amount of released BSA from Alg/Col hydrogels at 24 hr and 72 hr significantly decreased with increasing the alginate to collagen ratio. For instance, the amount of released BSA at 24 hr decreased significantly from 66.8% to 59.7% and 50.2% with changing the alginate to collagen weight ratio from 1/0.25 to 1/0.5, and 1/1. The amount of released BSA from Alg/Col hydrogels after 120 hr was over 90%. Also, alginate to collagen ratio did not significantly influence the amount of released BSA at 120 hr, 240 hr or 336 hr time points. The BMP2 release from alg/col hydrogels had a fast rate in the first 3 days in the range of 63.6% to 74.5% followed by a slower rate from day 3 to 14, accounting for 93.7% to 95.7% in total (FIG. 3H). The amount of released BMP2 from the alg/col hydrogels did not significantly change after day 14. At day 1 and day 3, the amount of released BMP2 from alg/col 1/0.25 hydrogel was significantly higher than the amount of BMP2 released from alg/col 1/0.5 or alg/col 1/1 hydrogels. After day 3, there was not a significant difference between the amount of BMP2 released from different hydrogels. Also, the released BMP2 from alg/col 1/0.5 and alg/col 1/1 hydrogels were not significantly different at any time point.

Figure 4D:
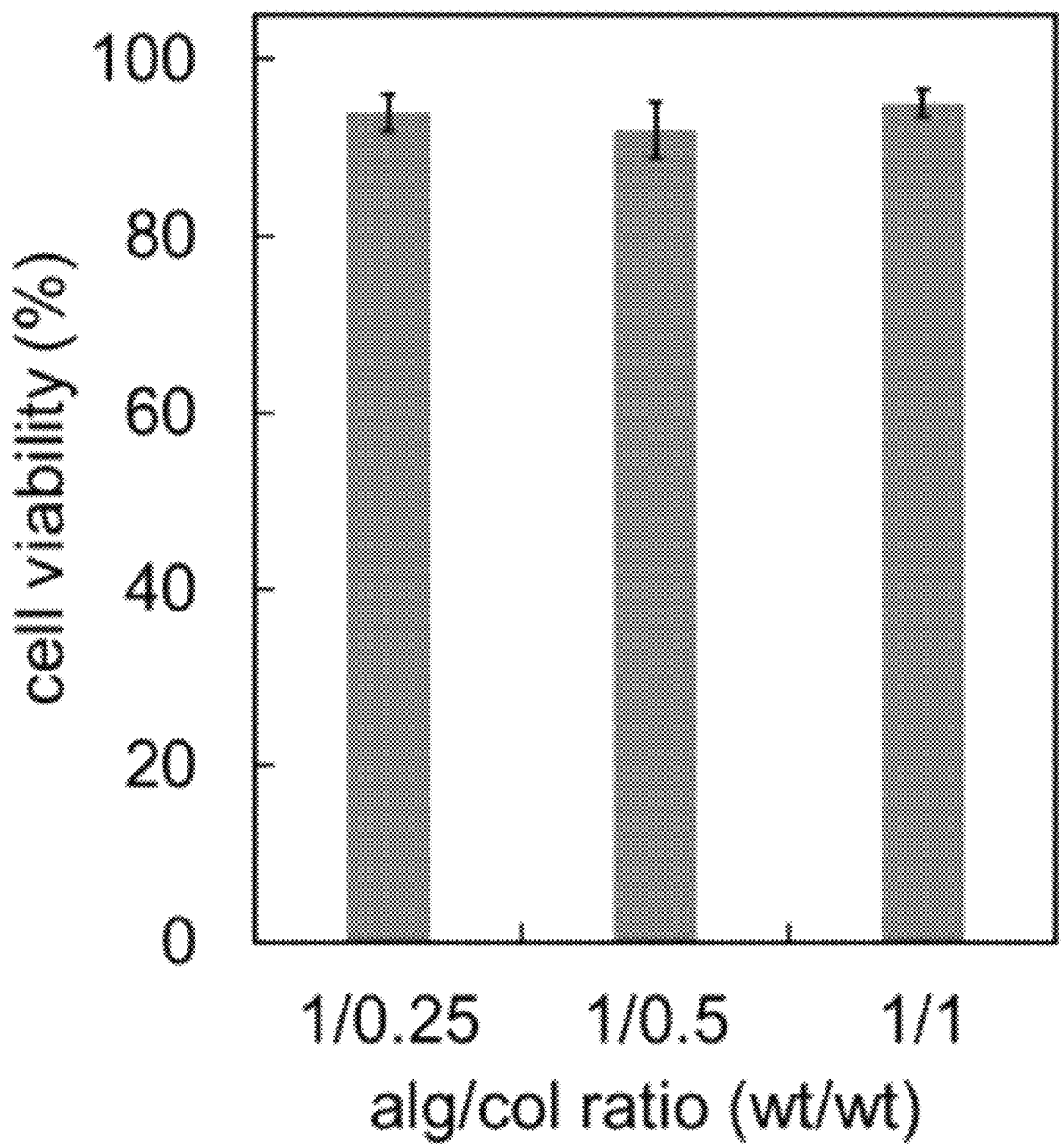
Figure 4E:
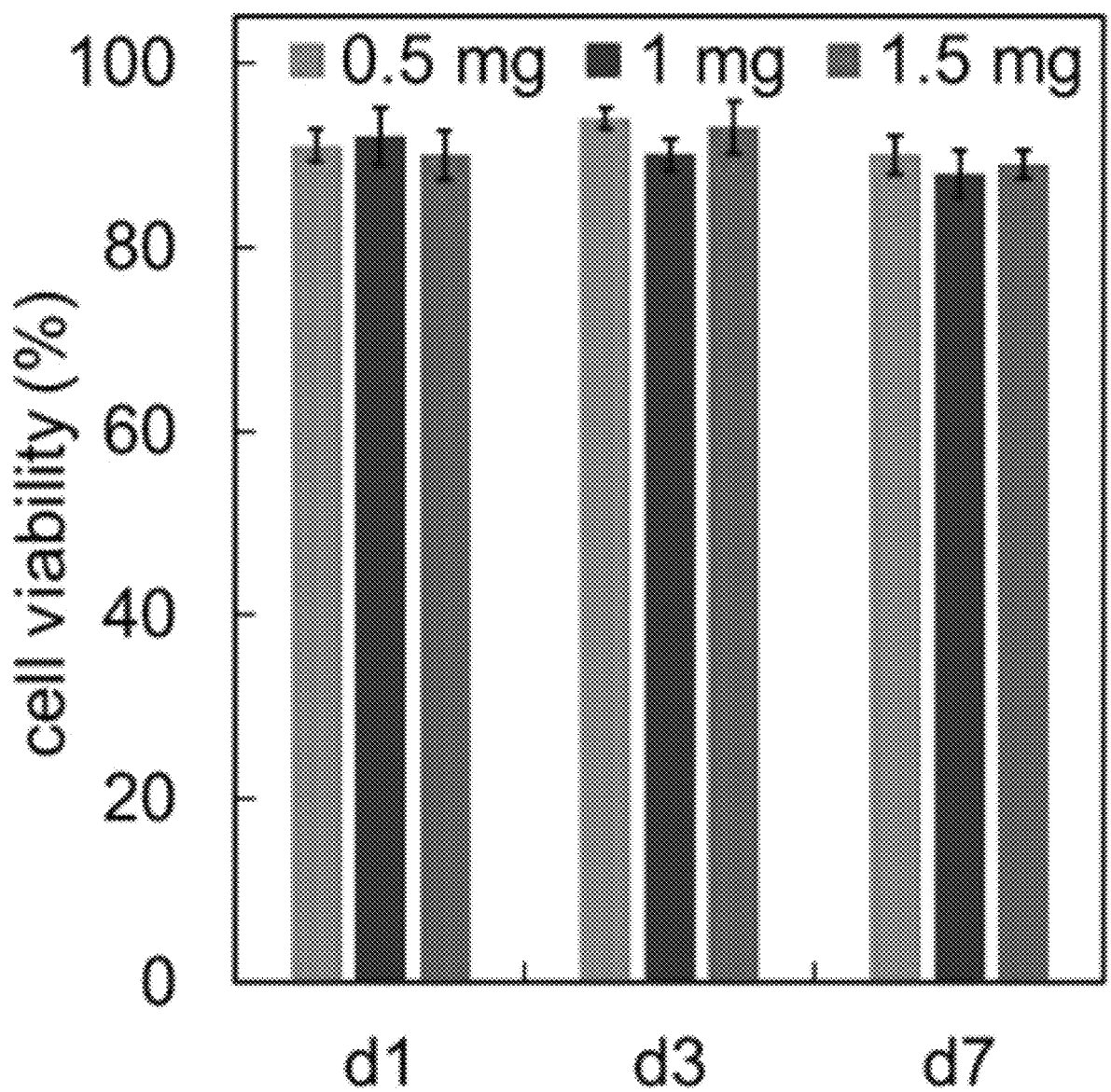
Figure 4F:
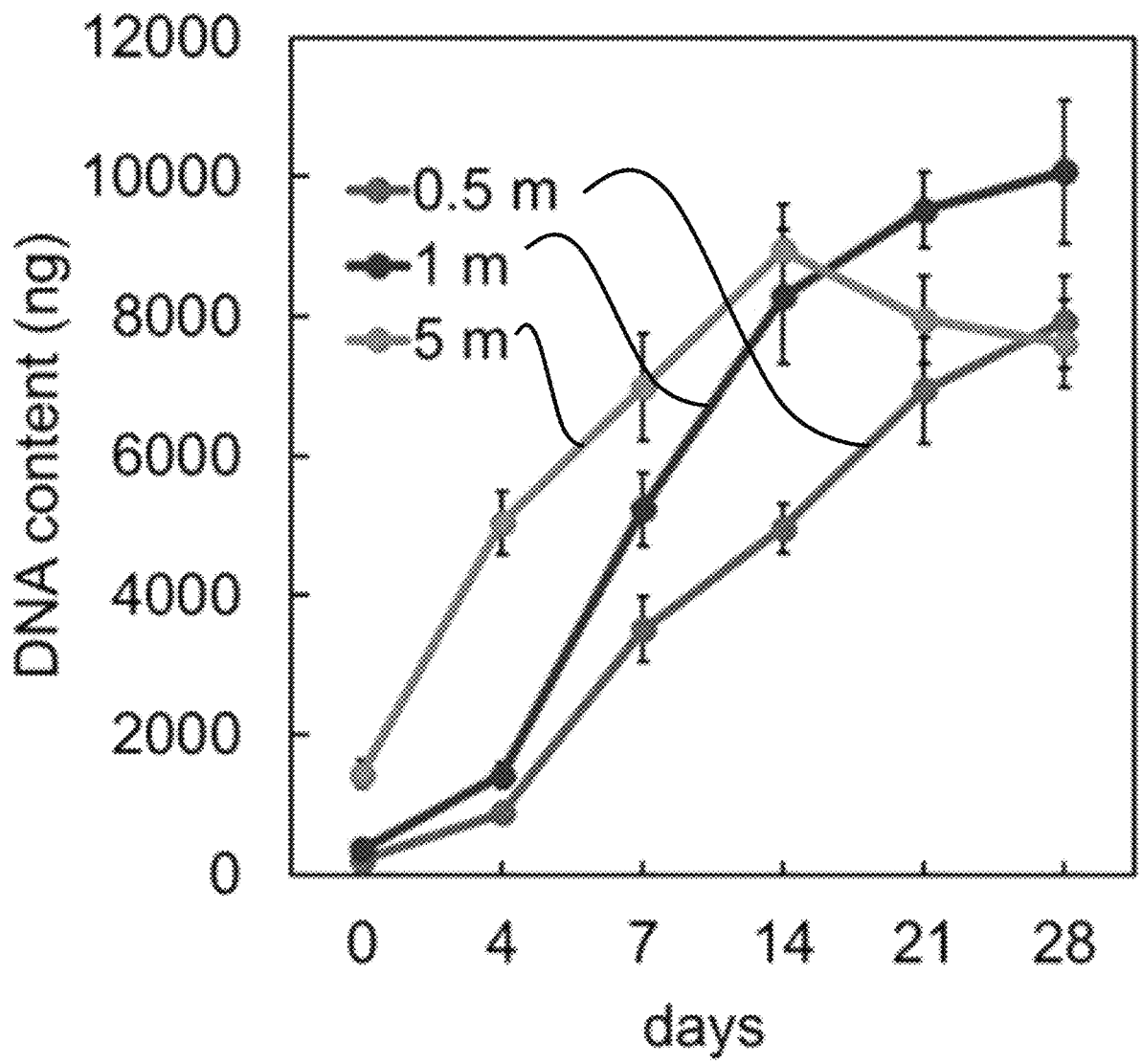

FIGS. 4A-C show images of live (green) and dead (orange) hMSCs encapsulated in Alg/Col 1/0.5 hydrogel with 0.5, 1 and 5 million cells/mL densities, respectively 24 hr after encapsulation. It is noted that the cell viability in these gels is high. Therefore, the number and intensity of orange dots (dead cells) are low. One might be able to see some bright orange dots in 4° C. though. The viability of hMSCs encapsulated in Alg/Col 1/0.5 hydrogel after 24 hr was 94%, 92%, and 93% for 0.5, 1 and 5 million cells/mL cell densities. The effect of alginate to collagen weight ratio on the viability of hMSCs encapsulated in Alg/Col hydrogel with 1 million cells/mL density after 24 hr is shown in FIG. 4D. The hMSC viability was 94%, 92%, and 95% for Alg/Col 1/0.25, Alg/Col 1/0.5, and Alg/Col 1/1 hydrogels, respectively. The variation in cell viability in Alg/Col hydrogels with changing the alginate to collagen ratio was not statistically significant. FIG. 4E shows the effect of $CaSO_4$ concentration in Alg/Col 1/0.5 hydrogels on the viability of encapsulated hMSCs. The viability of hMSCs encapsulated in Alg/Col 1/0.5 hydrogel with 0.5, 1 or 1.5 mg/mL $CaSO_4$ concentration did not significantly change from day 1 to 7. Further, a change in the $CaSO_4$ concentration from 0.5 to 1 or 1.5 mg/mL did not significantly affect the hMSC viability at day 1, 3 or 7. DNA content of hMSC-laden Alg/Col 1/0.5 hydrogels with cell densities of 0.5, 1 and 5 million cells/mL cultured in basal medium over 28 days is shown in FIG. 4F. When the density of hMSCs in Alg/Col hydrogel was 0.5 million cells/mL (0.5 m, blue line 410) the DNA content increased by 37.2 folds from day 0 to 28. The DNA content of Alg/Col hydrogel with 1 million encapsulated hMSCs/mL (1 m, red line 420) increased by 26.8 folds from day 0 to day 21 and then did not significantly change from day 21 to 28. The DNA content of Alg/Col hydrogel with 5 million hMSCs/mL (5 m, green line 430) initially increased by 6.2 folds from day 0 to 14 and then slightly dropped from day 14 to 28.

Figure 5A:
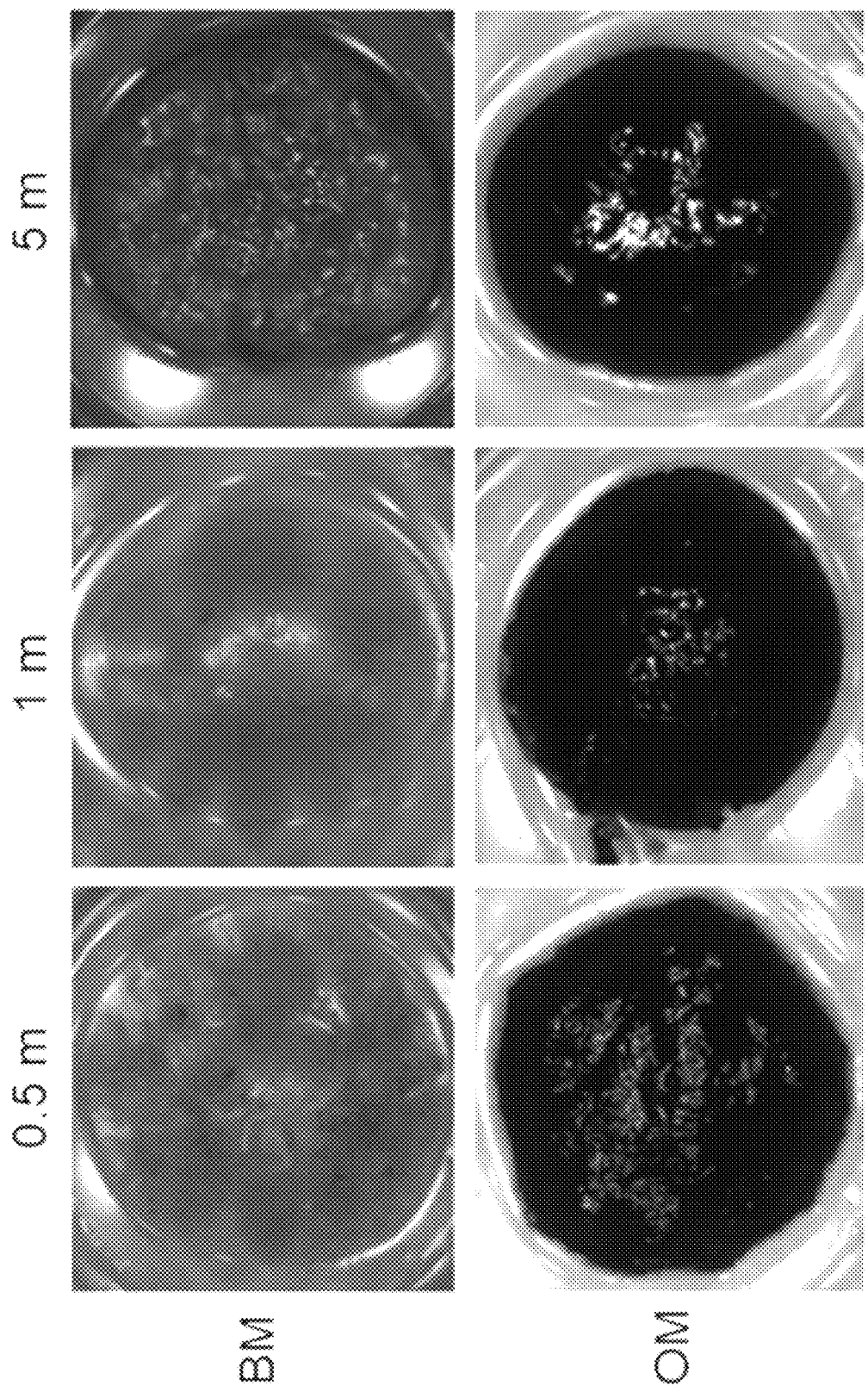
FIGS. 5A-C show according to an exemplary embodiment of the invention (FIG. 5A) Alizarin red stained hMSC-laden Alg/Col 1/0.5 hydrogels with 0.5, 1 and 5 million cells/mL densities and incubated in basal medium (BM) or osteogenic medium (OM) for 28 days, (FIG. 5B) ALP activity of hMSCs encapsulated in Alg/Col 1/0.5 hydrogels with 0.5, 1, or 5 million cells/mL density and incubated in BM or OM for 28 days, (FIG. 5C) calcium content of hMSCs-laden Alg/Col 1/0.5 hydrogels with 0.5, 1, or 5 million cells/mL density and incubated in BM or OM for 28 days. "An asterisk" represents a statistically significant difference between the test group and all other groups at that time point. Error bars correspond to means±1 SD for n=3.
Figure 5B:
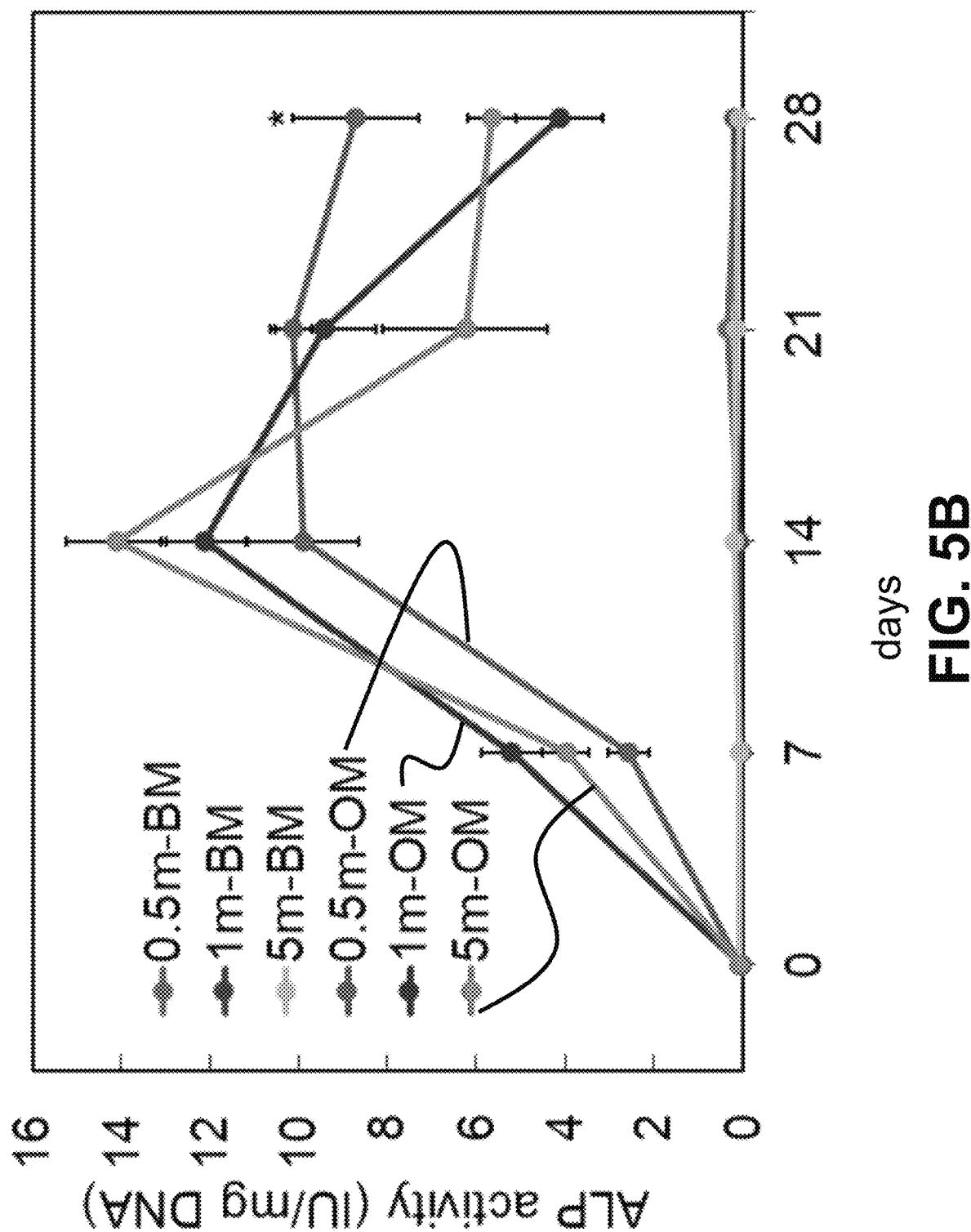

Images in FIG. 5A show Alizarin red stained hMSC-laden Alg/Col 1/0.5 hydrogels with 0.5, 1 and 5 million cells/mL densities and incubated in basal medium (BM) or osteogenic medium (OM) for 28 days. A significantly higher mineralization was observed in hMSC-laden hydrogel groups that were incubated in OM compared to those incubated in BM. ALP activity of hMSCs encapsulated in Alg/Col 1/0.5 hydrogels with 0.5, 1, or 5 million cells/mL density and incubated in BM or OM for 28 days is shown in FIG. 5B. The ALP activity of hMSCs did not significantly change when the cell-laden Alg/Col hydrogels were incubated in BM. The ALP activity of hMSCs encapsulated in Alg/Col hydrogels and incubated in OM drastically increased from day 0 to 14 and then either dropped (for 1 and 5 million cells/mL densities) or did not significantly change (for 0.5 million cells/mL density) from day 14 to 28.

Figure 5C:
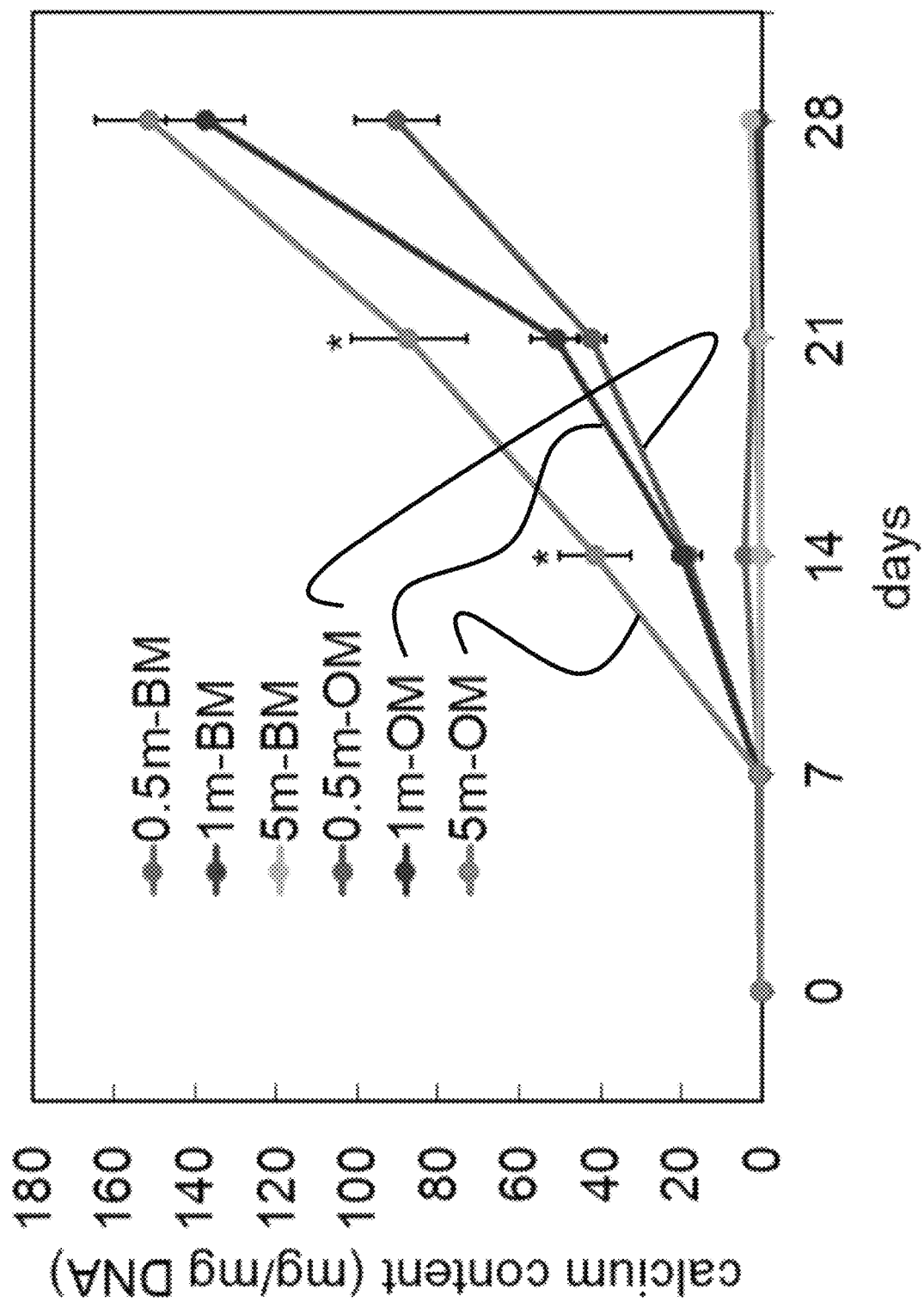

Calcium content of Alg/Col 1/0.5 hydrogels loaded with 0.5, 1, or 5 million hMSCs/mL and incubated in BM or OM for 28 days is shown in FIG. 5C. The calcium content of hydrogel samples did not significantly change when the hMSC-laden Alg/Col hydrogels were incubated in BM, regardless of cell density. The calcium content of those hMSC-laden hydrogels that were incubated in OM did not change initially from day 0 to 7, then significantly increased from day 7 to 28. The calcium content of hMSC-laden hydrogels with 1 or 5 million cells/mL cell density was significantly higher than that of hMSC-laden hydrogels with 0.5 million cells/mL after 28 days of incubation in OM.

Figure 6A:
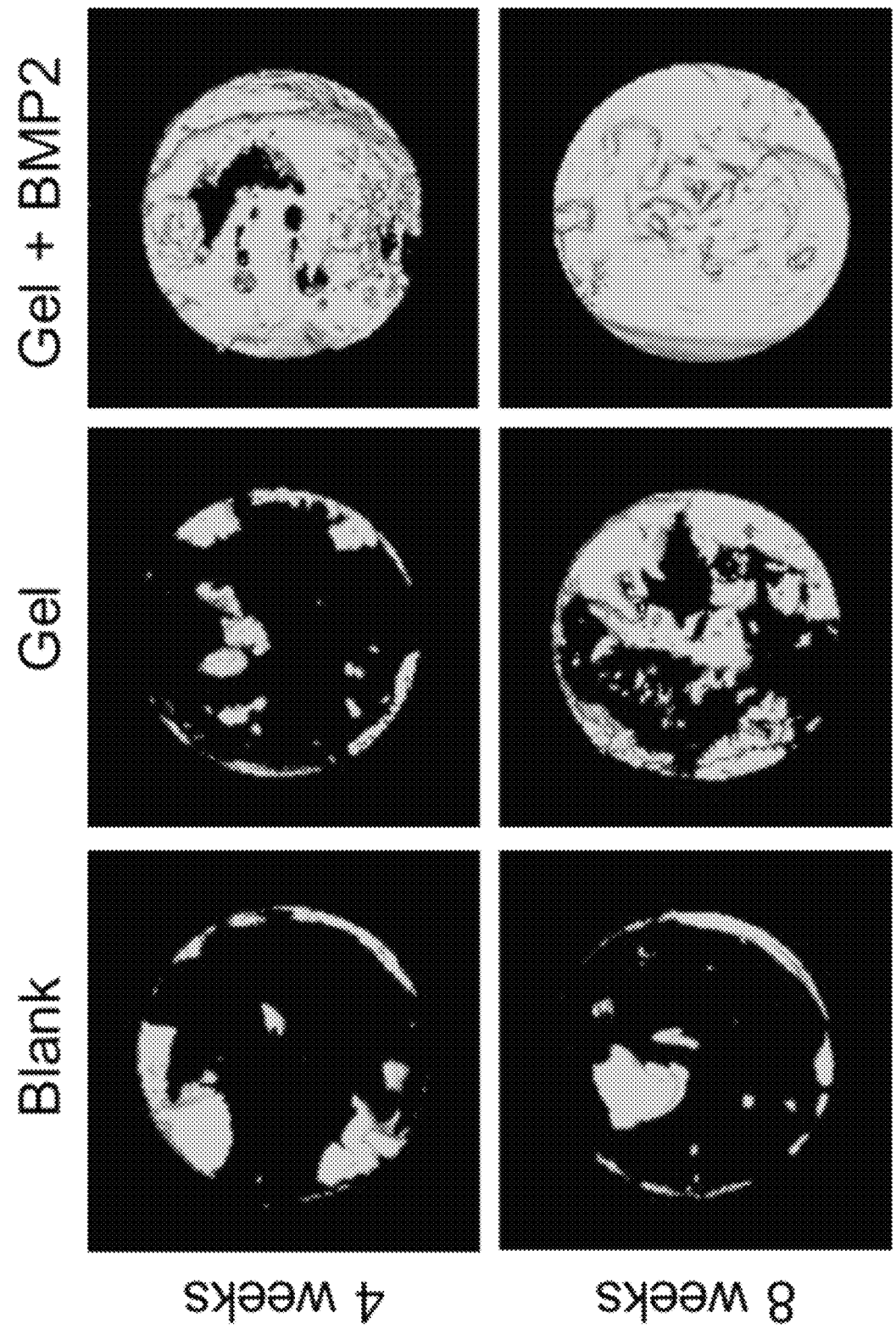
FIGS. 6A-B show according to an exemplary embodiment of the invention representative micro-CT reconstructed 3D images and the quantitative result of regenerated bone in the calvarial defect site.
Figure 6B:
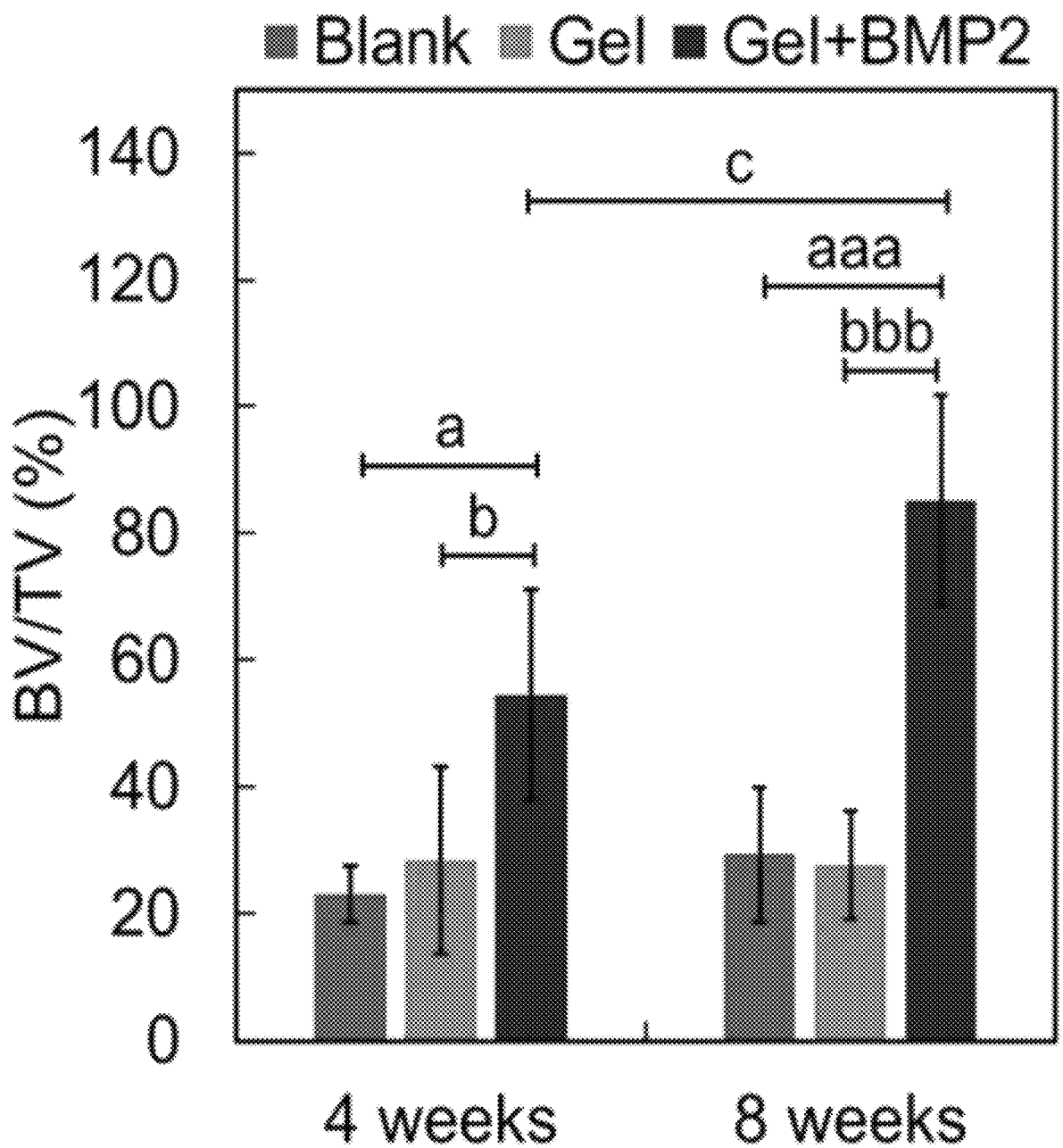

The efficacy of the BMP2-incorporated Alg/Col 1/0.5 hydrogel in calvarial bone defect healing was assessed by micro-CT analysis at 4 weeks or 8 weeks after implantation. From the 3D reconstructed results, the inventors found only small amount of new bone regenerated from the cutting edges in the blank control group and in the hydrogel only group at 4 weeks or 8 weeks (FIG. 6A). The hydrogel alone showed no significant effect on bone healing compared with blank controls (FIGS. 6A-B). However, the hydrogel loaded with BMP2 promoted calvarial bone healing significantly, with 135.8% (P<0.05) or 190.8% (P<0.001) increase in bone volume fraction (BV/TV) after 4 weeks or 8 weeks respectively, compared with the blank control group. In addition, the bone volume fraction of BMP2-laden hydrogel group was 91.3% (P<0.05) or 207.8% (P<0.001) higher after 4 weeks or 8 weeks, compared with that of the hydrogel only group (FIGS. 6A-B). After 8 weeks of BMP2-laden hydrogel injection, the calvarial bone defect nearly healed, with a 56.3% (P<0.05) increase in BV/TV compared with that after 4 weeks of injection (FIGS. 6A-B).

Figure 7:
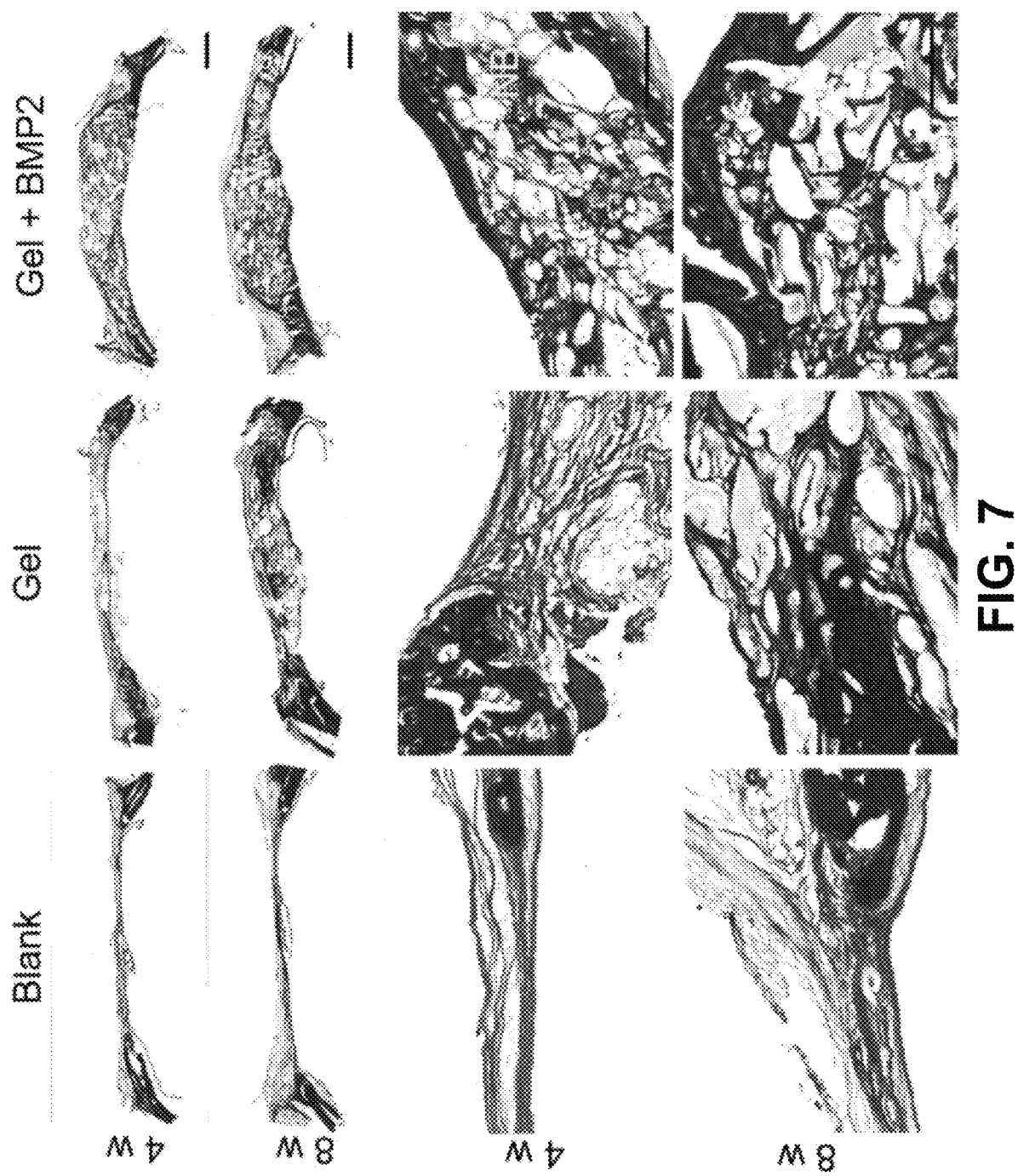
FIG. 7 shows according to an exemplary embodiment of the invention trichrome staining images of newly regenerated tissue in calvarial defect sites without hydrogel injection (Blank) or with injection of Alg/Col 1/0.5 hydrogel alone (Gel) or BMP2-loaded Alg/Col 1/0.5 hydrogel (Gel+BMP2) after 4 weeks or 8 weeks. Porous structure indicates hydrogel area. NB: new bone.

Histological results (FIG. 7) showed regenerated tissue in the calvarial defect sites and an integration of newly formed tissue with the existing native tissue at 4 or 8 weeks after implantation. From the results of Trichrome and H & E staining, the inventors found the defect sites were mainly covered with fibrous tissue and a few small bone islands in the blank control group or hydrogel only group (Alg/Col 1/0.5 hydrogel) at 4 or 8 weeks after operation (FIG. 7). A large amount of newly formed bone with seamless integration to the native tissue at the defect sites was found in the BMP2-incorporated hydrogel (Alg/Col 1/0.5 hydrogel) group at 4 or 8 weeks after operation (FIG. 7). The newly formed bone in the later time point (8 weeks) was more mature than that at the early time point (4 weeks). This result was consistent with the data from micro-CT analysis, which showed a better bone healing effect in the BMP2-incorporated hydrogel group, especially at the later time point (8 weeks). Osteogenic markers including osteocalcin (OCN) and osteopontin (OPN) were measured by immunohistochemistry (FIGS. 8A-C). As shown by the results, the expression levels of OCN and OPN were relatively low in the blank control group or hydrogel only group (Alg/Col 1/0.5 hydrogel) at 4 or 8 weeks after operation (FIGS. 8A-C). However, significantly higher expression levels were found in the BMP2-laden hydrogel group, with 327.2% (P<0.001) or 228.6% (P<0.001) increase in percentage of OCN positive area, and 407.5% (P<0.001) or 243.4% (P<0.001) increase in percentages of OPN positive area after 4 weeks or 8 weeks, respectively, compared with the blank control group (FIGS. 8B-C). In addition, when compared with the hydrogel only group, the BMP2-laden hydrogel group had 285.5% (P<0.05) or 228.6% (P<0.001) higher percentage of OCN positive area, and 160.9% (P<0.001) or 208.5% (P<0.001) higher percentage of OPN positive area after 4 weeks or 8 weeks (FIGS. 8B-C).

What is claimed is:

1. A delivery platform kit for cells or therapeutics, wherein the delivery platform kit comprises a first liquid container and a second liquid container, comprising:
   (a) the first liquid container in the delivery platform kit comprising a first liquid, wherein the first liquid is an alginate precursor liquid stored at a temperature of about 4° C., wherein the alginate precursor liquid is dissolved in a calcium free medium and a basic pH medium, and wherein the calcium free medium is defined as without calcium salts and $Ca^{2+}$ ions; and
   (b) the second liquid container in the delivery platform kit comprising a second liquid, wherein the second liquid is a collagen and $CaSO_4$ precursor liquid stored at a temperature of about 4° C., wherein the collagen and $CaSO_4$ precursor liquid is dissolved in a calcium free medium and an acidic medium, wherein the calcium free medium is defined as without calcium salts or $Ca^{2+}$ ions.

2. The delivery platform as set forth in claim 1, wherein the calcium free and basic pH medium is defined as a pH higher than physiological pH (7.4).

3. The delivery platform as set forth in claim 1, wherein the calcium free and acidic medium is defined as a pH lower than physiological pH (7.4).

4. The delivery platform as set forth in claim 1, wherein the first liquid container, the second liquid container, or both further comprising cells, therapeutics, or a combination thereof.

5. The delivery platform as set forth in claim 1, wherein the supplemented $CaSO_4$ is in the range of 1-10 mg/mL.

6. The delivery platform as set forth in claim 1, wherein the alginate in the alginate precursor liquid in the first liquid container and the collagen in the collagen and $CaSO_4$ precursor liquid in the second liquid container have a weight ratio ranging from 1/10 to 10/1.

* * * * *